United States Patent
George et al.

(10) Patent No.: US 11,659,998 B2
(45) Date of Patent: *May 30, 2023

(54) AUTOMATIC MEASUREMENT USING STRUCTURED LIGHTS

(71) Applicant: International Business Machines Corporation, Armonk, NY (US)

(72) Inventors: Yasmeen Mourice George, Melbourne (AU); Lenin Mehedy, Doncaster East (AU); Rahil Garnavi, Macleod (AU)

(73) Assignee: International Business Machines Corporation, Armonk, NY (US)

( * ) Notice: Subject to any disclaimer, the term of this patent is extended or adjusted under 35 U.S.C. 154(b) by 522 days.

This patent is subject to a terminal disclaimer.

(21) Appl. No.: 16/809,610

(22) Filed: Mar. 5, 2020

(65) Prior Publication Data

US 2021/0275026 A1 Sep. 9, 2021

(51) Int. Cl.
*A61B 5/00* (2006.01)
*G06T 7/00* (2017.01)
(Continued)

(52) U.S. Cl.
CPC ............ *A61B 5/0064* (2013.01); *A61B 5/004* (2013.01); *A61B 5/441* (2013.01); *A61B 5/445* (2013.01); *G06T 7/0012* (2013.01); *G06T 7/60* (2013.01); *G06T 7/62* (2017.01); *G16H 30/40* (2018.01); *G16H 50/20* (2018.01); *G16H 50/30* (2018.01);
(Continued)

(58) Field of Classification Search
CPC ....... A61B 5/0064; A61B 5/004; A61B 5/445; A61B 5/0075; A61B 5/441; A61B 5/6898; A61B 5/7267; G06T 7/0012; G06T 7/60; G06T 2207/10052; G06T 2207/30088; G06T 2207/10028; G06T 2207/20084;
(Continued)

(56) References Cited

U.S. PATENT DOCUMENTS 8,755,577 B2 6/2014 Mohamad Hani et al.
9,962,089 B2 5/2018 Mohamad Hani et al.
(Continued)

FOREIGN PATENT DOCUMENTS

EP 2389573 B1 1/2016
WO 2004034888 A2 4/2004
(Continued)

OTHER PUBLICATIONS

Deepthi, "Time-Of-Flight Laser for Presto Measurements of Wound Depth", International Journal of Advanced Science and Technology, vol. 29, No. 02, 2020 p. 2452-2459; 9p.
(Continued)

*Primary Examiner* — Ping Y Hsieh
*Assistant Examiner* — Daniella M. DiGuglielmo
(74) *Attorney, Agent, or Firm* — Cantor Colburn LLP; Michael A. Petrocelli

(57) ABSTRACT

Techniques for automatic measurement using structured lights are provided. A computer system uses structured lights to acquire skin information, the skin information being associated with at least one affected area of the skin. The computer system determines parameters related to the at least one affected area of the skin, at least partly, on the skin information and generates an assessment for the at least one affected area of the skin.

13 Claims, 18 Drawing Sheets

(51) Int. Cl.
| | |
|---|---|
| *G16H 50/30* | (2018.01) |
| *G06T 7/60* | (2017.01) |
| *G16H 30/40* | (2018.01) |
| *G16H 50/20* | (2018.01) |
| *G06T 7/62* | (2017.01) |

(52) U.S. Cl.
CPC .......... *A61B 5/0075* (2013.01); *A61B 5/6898* (2013.01); *A61B 5/7267* (2013.01); *G06T 2207/10028* (2013.01); *G06T 2207/10052* (2013.01); *G06T 2207/20084* (2013.01); *G06T 2207/30088* (2013.01)

(58) Field of Classification Search
CPC .......... G06T 7/62; G16H 50/30; G16H 30/40; G16H 50/20
See application file for complete search history.

(56) References Cited

U.S. PATENT DOCUMENTS

| | | | |
|---|---|---|---|
| 10,130,297 | B2 | 11/2018 | Schnidar et al. |
| 2008/0172114 | A1* | 7/2008 | Gourgouliatos ..... A61N 5/0624 607/94 |
| 2011/0218428 | A1* | 9/2011 | Westmoreland ......... A61B 6/00 600/425 |
| 2012/0308096 | A1* | 12/2012 | Mohamad Hani .... G06T 7/0012 382/128 |
| 2013/0018271 | A1* | 1/2013 | Mohamad Hani ........ G06T 7/60 600/476 |
| 2015/0150457 | A1 | 6/2015 | Wu et al. |
| 2016/0058288 | A1 | 3/2016 | Debarnadis et al. |
| 2017/0000351 | A1* | 1/2017 | Fright .................. A61B 5/0077 |
| 2017/0061621 | A1 | 3/2017 | Wortman et al. |
| 2018/0338710 | A1 | 11/2018 | Tas et al. |
| 2019/0125247 | A1 | 5/2019 | Saeki et al. |
| 2019/0239729 | A1 | 8/2019 | Lim et al. |
| 2021/0174512 | A1 | 6/2021 | Chen et al. |

FOREIGN PATENT DOCUMENTS

| | | | | |
|---|---|---|---|---|
| WO | WO-2004034888 A2 | * | 4/2004 | ............. A61B 5/441 |
| WO | WO-2018171851 A1 | * | 9/2018 | ......... A61B 1/00009 |

OTHER PUBLICATIONS

Gaur, "Efficient wound measurements using RGB and depth images", Int. J. Biomedical Engineering and Technology, vol. 18, No. 4, 2015; 26 p.
trustreviews.com; "Intel RealSense Camera Review", Jan. 9, 2014, 6p.
Randeberg, "Combined hyperspectral and #D characterization of non-healing skin ulcers"; IEEE 2013 Color and Visual Computing Symposium (CVCS); Oct. 10, 2013; 7 pages.
Occipital Inc. "What are the technical specifications of Structure Sensor (ST01)?" Nov. 4, 2020; 2 pages.
List of IBM Patents or Patent Applications Treated as Related; (Appendix P); Date Filed: Mar. 5, 2020, 2 pages.
Yasmeen Mourice George et al., "Automatic Association Between Physical and Visual Skin Properties," U.S. Appl. No. 16/809,609, filed Mar. 5, 2020.
Feldman, "Psoriasis assessment tools in clinical trials", Ann Rheum Dis; Feb. 11, 2005; 4 pages.
Garza, "A dynamic model for prediction of psoriasis management by blue light irradiation" Frontiers in physiology, vol. 8, Article28, Jan. 26, 2017, 17 pages.
Morsy, "Optical coherence tomography imaging of psoriasis vulgaris: correlation with histology and disease severity" Archives of dermatological research, Nov. 6, 2009, 7 pages.
Myers, "Capturing depth: structured light, time of fl ight, andthe future of 3D imaging", AndroidAuthority.com; Jun. 22, 2018; 9 pages.
Park, "Quantitative evaluation of severity in psoriatic lesions using three-dimensional morphometry", Experimental dermatology, 2004: 13: 223-228, 6 pages.
Samarasekera, "Assessment and management of psoriasis: summary of NICE guidance", Bmj, vol. 345, Oct. 27, 2012; 6 pages.
Webster, "Structured Light Techniques and Applications", Wiley Encyclopedia of Electrical and Electronics Engineering, 2016; 24 pages.

* cited by examiner

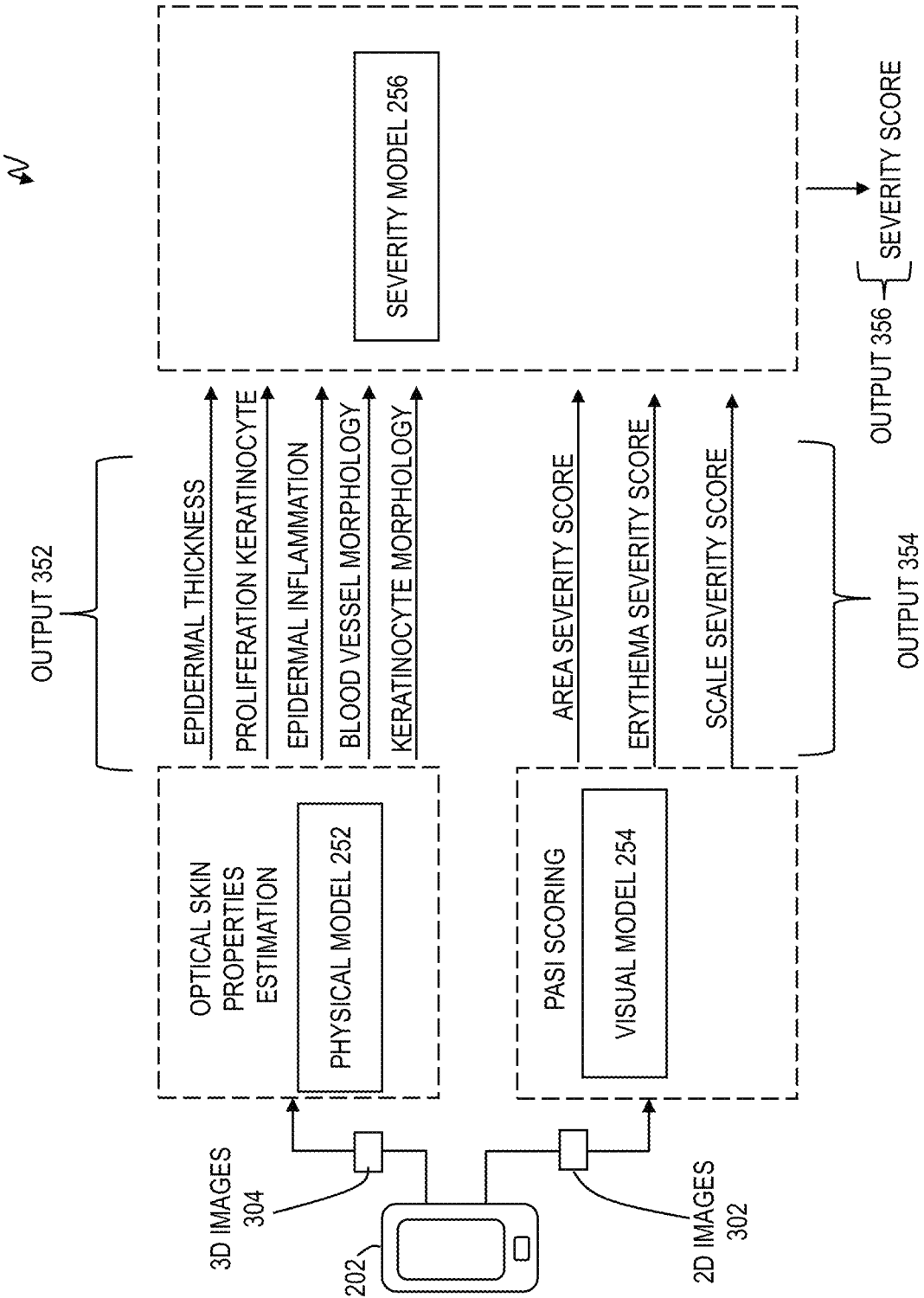

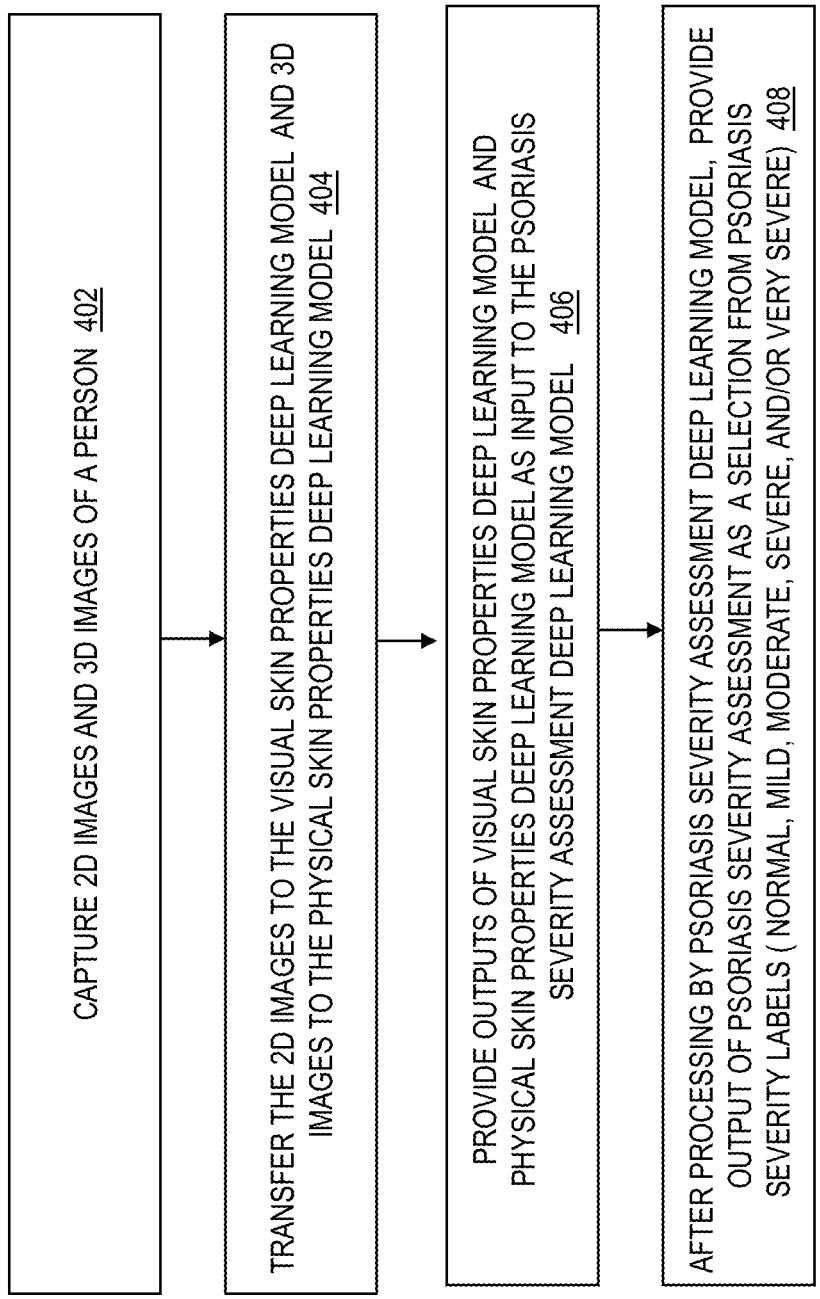

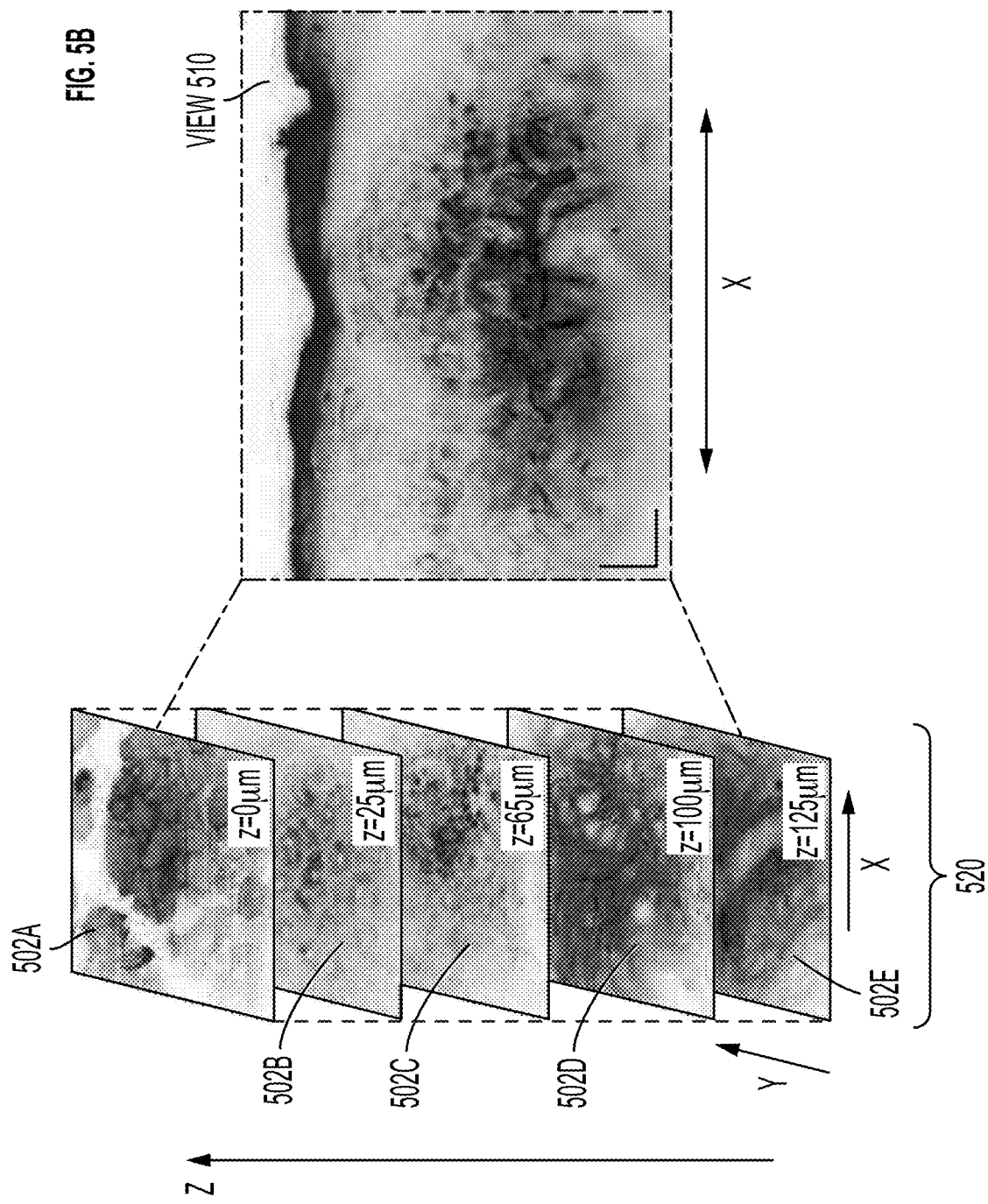

AUTOMATIC MEASUREMENT USING STRUCTURED LIGHTS

BACKGROUND

The present invention generally relates to computer systems, and more specifically, to computer systems, computer program products, and computer-implemented methods for automatic measurement using structured lights.

In computer science, digital image processing is the use of a digital computer to process digital images through an algorithm. Digital image processing includes image capture and image processing of the captured images. Image sensors are used to capture the digital images. The basis for modern image sensors is metal-oxide-semiconductor (MOS) technology, and particularly, the charge-coupled device (CCD) which is the basis for the complimentary metal-oxide-semiconductor CMOS sensor. Image processing uses a set of computational techniques for analyzing, enhancing, compressing, and reconstructing images. Its main components are importing, in which an image is captured through scanning or digital photography, along with analysis and manipulation of the image, accomplished using various specialized software applications and models. The images are also output, for example, to a screen or monitor. As a result of advances in image capturing and image processing, computers use images and image processing in the medical field to assist with detection of disease states.

SUMMARY

Embodiments of the present invention are directed to automatic measurement using structured lights. A non-limiting example computer-implemented method includes using, by a computer system, structured lights to acquire skin information of the skin, the skin information being associated with at least one affected area of the skin. The method includes determining, by the computer system, parameters related to the at least one affected area of the skin based, at least partly, on the skin information. Also, the method includes generating, by the computer system, an assessment for the at least one affected area.

Additionally and/or alternatively in one or more embodiments of the invention, a border of the at least one affected area is determined based on the skin information.

Additionally and/or alternatively in one or more embodiments of the invention, a chromatic change in the structured lights provides skin information for the at least one affected area.

Additionally and/or alternatively in one or more embodiments of the invention, a three-dimensional (3D) image is obtained using the structured lights.

Additionally and/or alternatively in one or more embodiments of the invention, the parameters related to the at least one affected area include an area value.

Additionally and/or alternatively in one or more embodiments of the invention, the parameters related to the at least one affected area include an induration value.

Additionally and/or alternatively in one or more embodiments of the invention, the parameters related to the at least one affected area include a scale value.

Additionally and/or alternatively in one or more embodiments of the invention, the parameters related to the at least one affected area include an erythema value.

Additionally and/or alternatively in one or more embodiments of the invention, the assessment for the at least one affected area comprises a psoriasis severity assessment.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 3B is a block diagram of further details of models in the system for automatic association between physical/inner skin properties and visual/surface skin properties to provide the assessment in accordance with one or more embodiments of the present invention;

FIG. 4 is a flow diagram of a process for automatically determining an association between physical/inner skin properties and visual/surface skin properties to provide the comprehensive skin disorder severity assessment in accordance with one or more embodiments of the present invention;

FIG. 5B illustrates an example of three-dimensional (3D) imaging of skin according to one or more embodiments of the invention;

DETAILED DESCRIPTION

One or more embodiments of the present invention provide computer-implemented methods for skin disorder severity assessment using red, green, and blue (RGB) images by measuring visual/surface skin parameters combined with three-dimensional (3D) skin images by measuring one or two (or more) physical/inner skin parameters, using, for example, a smartphone. Accordingly, the association between these two sets of parameters, visual and physical, is utilized jointly for accurate assessment of skin disorder severity according to embodiments of the invention. Moreover, embodiments of the invention provide an accurate, comprehensive, and multimodal skin disorder severity scoring that automatically learns the association between physical/inner and visual/surface skin parameters for severity scoring. In some embodiments of the invention, the skin disorder is psoriasis, and the skin parameters are psoriasis parameters.

In some embodiments of the invention, 3D skin images are generated using structured light in a structured lighting process. Structured light is light having a known pattern, including, for example, lines, grids, bars, and the like. Structured light is used in structured lighting processes to create three-dimensional (3D) objects and measure distances in an observed scene. In an example structured lighting process, structured light having a known light pattern (e.g., grids and/or horizontal bars) is projected onto an area of skin. The structured light will deform when striking surfaces, which allows a vision system (e.g., a camera) to capture the deformed structured light and calculate therefrom depth and surface information of any 3D topology that is present on the skin and struck by the structured light.

Figure 1:
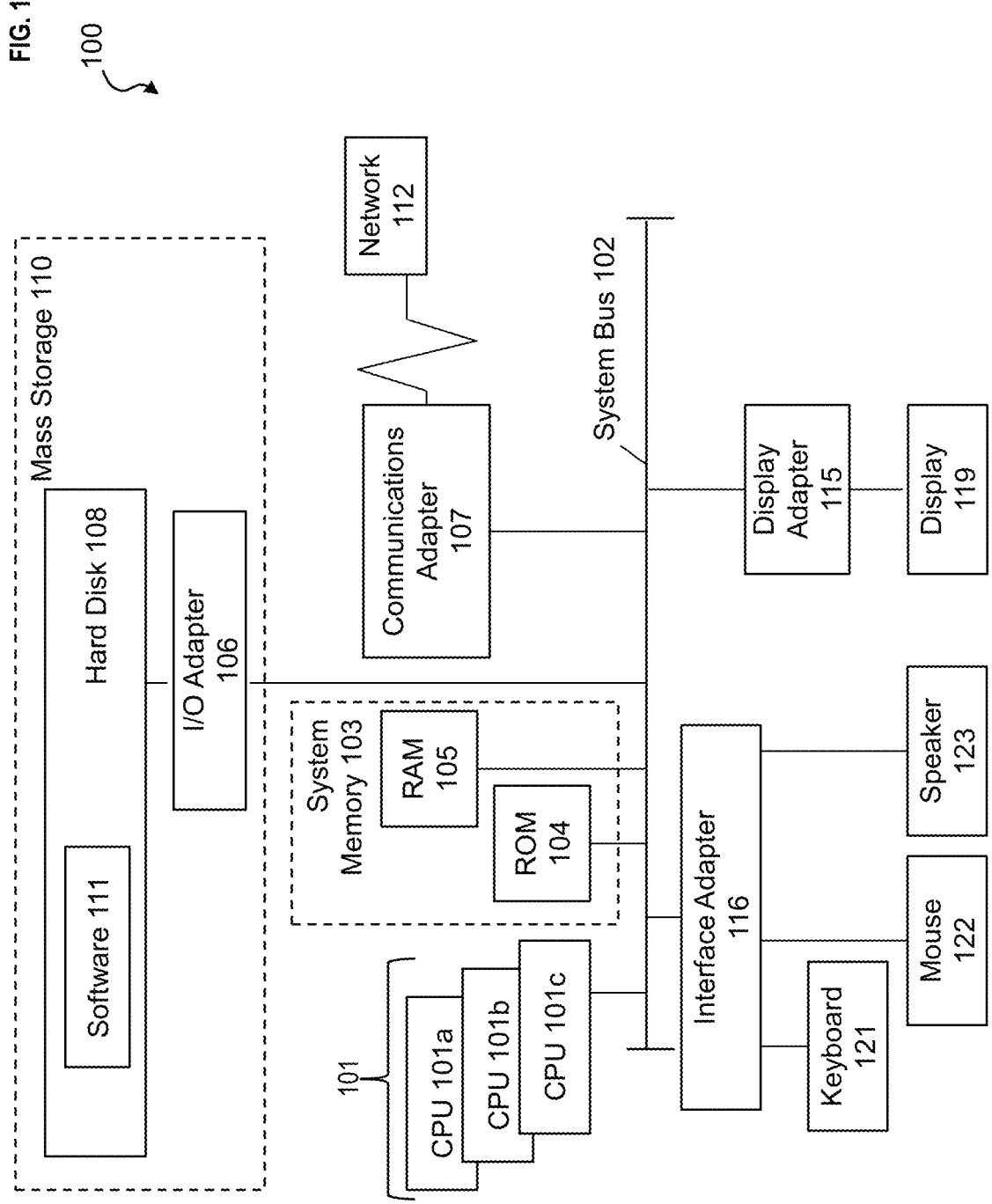
FIG. 1 is a block diagram of an example computer system for use in conjunction with one or more embodiments of the present invention.

Turning now to FIG. 1, a computer system 100 is generally shown in accordance with one or more embodiments of the invention. The computer system 100 can be an electronic, computer framework comprising and/or employing any number and combination of computing devices and networks utilizing various communication technologies, as described herein. The computer system 100 can be easily scalable, extensible, and modular, with the ability to change to different services or reconfigure some features independently of others. The computer system 100 can be, for example, a server, desktop computer, laptop computer, tablet computer, or smartphone. In some examples, computer system 100 can be a cloud computing node. Computer system 100 can be described in the general context of computer system executable instructions, such as program modules, being executed by a computer system. Generally, program modules can include routines, programs, objects, components, logic, data structures, and so on that perform particular tasks or implement particular abstract data types. Computer system 100 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 1, the computer system 100 has one or more central processing units (CPU(s)) 101a, 101b, 101c, etc., (collectively or generically referred to as processor(s) 101). The processors 101 can be a single-core processor, multi-core processor, computing cluster, or any number of other configurations. The processors 101, also referred to as processing circuits, are coupled via a system bus 102 to a system memory 103 and various other components. The system memory 103 can include a read only memory (ROM) 104 and a random access memory (RAM) 105. The ROM 104 is coupled to the system bus 102 and can include a basic input/output system (BIOS), which controls certain basic functions of the computer system 100. The RAM is read-write memory coupled to the system bus 102 for use by the processors 101. The system memory 103 provides temporary memory space for operations of said instructions during operation. The system memory 103 can include random access memory (RAM), read only memory, flash memory, or any other suitable memory systems.

The computer system 100 comprises an input/output (I/O) adapter 106 and a communications adapter 107 coupled to the system bus 102. The I/O adapter 106 can be a small computer system interface (SCSI) adapter that communicates with a hard disk 108 and/or any other similar component. The I/O adapter 106 and the hard disk 108 are collectively referred to herein as a mass storage 110.

Software 111 for execution on the computer system 100 can be stored in the mass storage 110. The mass storage 110 is an example of a tangible storage medium readable by the processors 101, where the software 111 is stored as instructions for execution by the processors 101 to cause the computer system 100 to operate, such as is described herein below with respect to the various Figures. Examples of computer program product and the execution of such instruction is discussed herein in more detail. The communications adapter 107 interconnects the system bus 102 with a network 112, which can be an outside network, enabling the computer system 100 to communicate with other such systems. In one embodiment, a portion of the system memory 103 and the mass storage 110 collectively store an operating system, which can be any appropriate operating system, such as the z/OS or AIX operating system from IBM Corporation, to coordinate the functions of the various components shown in FIG. 1.

Additional input/output devices are shown as connected to the system bus 102 via a display adapter 115 and an interface adapter 116. In one embodiment, the adapters 106, 107, 115, and 116 can be connected to one or more I/O buses that are connected to the system bus 102 via an intermediate bus bridge (not shown). A display 119 (e.g., a screen or a display monitor) is connected to the system bus 102 by the display adapter 115, which can include a graphics controller to improve the performance of graphics intensive applications and a video controller. A keyboard 121, a mouse 122, a speaker 123, etc., can be interconnected to the system bus 102 via the interface adapter 116, which can include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 1, the computer system 100 includes processing capability in the form of the processors 101, and, storage capability including the system memory 103 and the mass storage 110, input means such as the keyboard 121 and the mouse 122, and output capability including the speaker 123 and the display 119.

In some embodiments, the communications adapter 107 can transmit data using any suitable interface or protocol, such as the internet small computer system interface, among others. The network 112 can be a cellular network, a radio network, a wide area network (WAN), a local area network (LAN), or the Internet, among others. An external computing device can connect to the computer system 100 through the network 112. In some examples, an external computing device can be an external webserver or a cloud computing node.

It is to be understood that the block diagram of FIG. 1 is not intended to indicate that the computer system 100 is to include all of the components shown in FIG. 1. Rather, the computer system 100 can include any appropriate fewer or additional components not illustrated in FIG. 1 (e.g., additional memory components, embedded controllers, modules, additional network interfaces, etc.). Further, the embodiments described herein with respect to computer system 100 can be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

Figure 2:
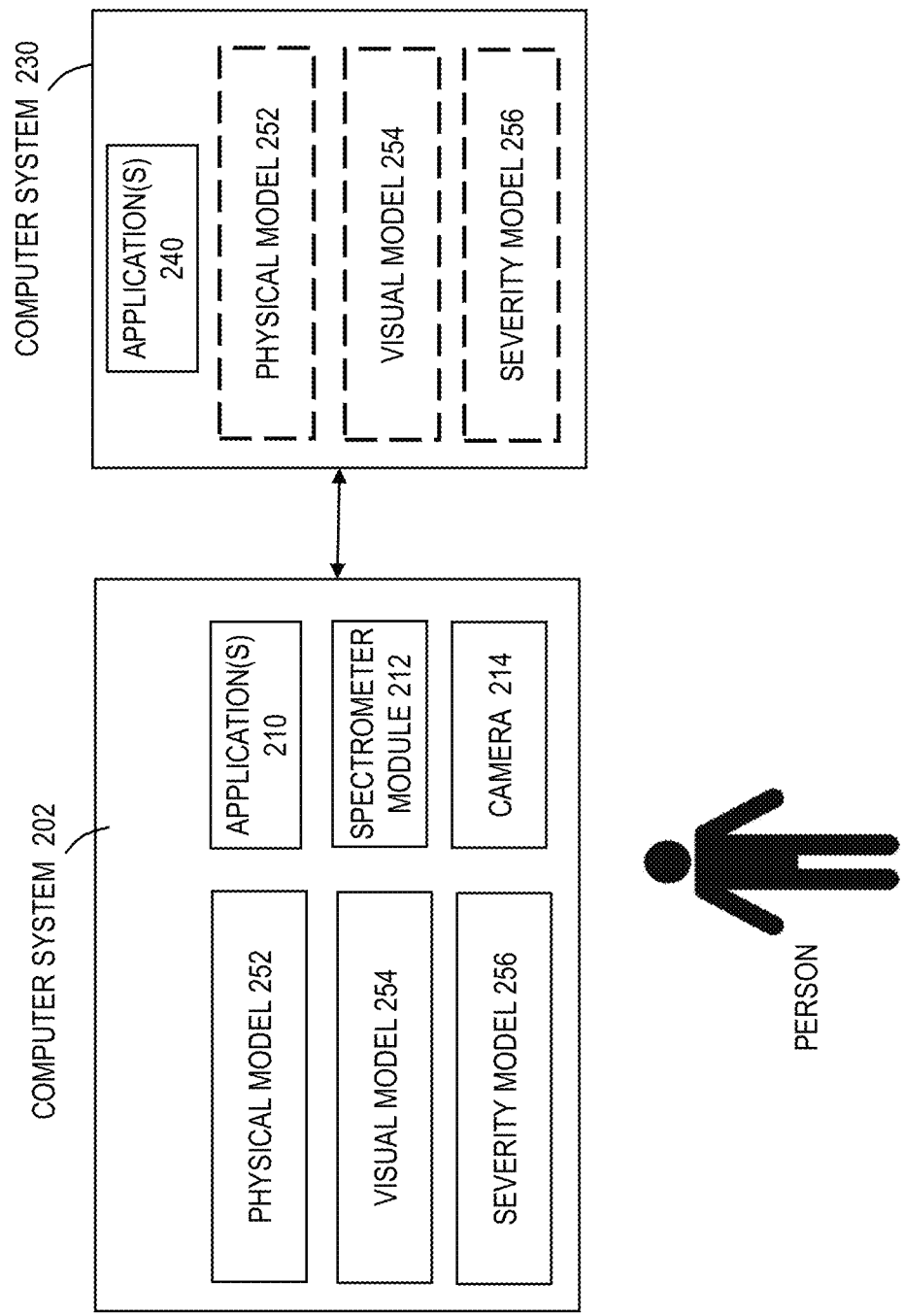
FIG. 2 is a block diagram of an example system for automatic association between physical/inner skin properties and visual/surface skin properties to provide a comprehensive skin disorder severity assessment in accordance with one or more embodiments of the present invention.
Figure 3A:
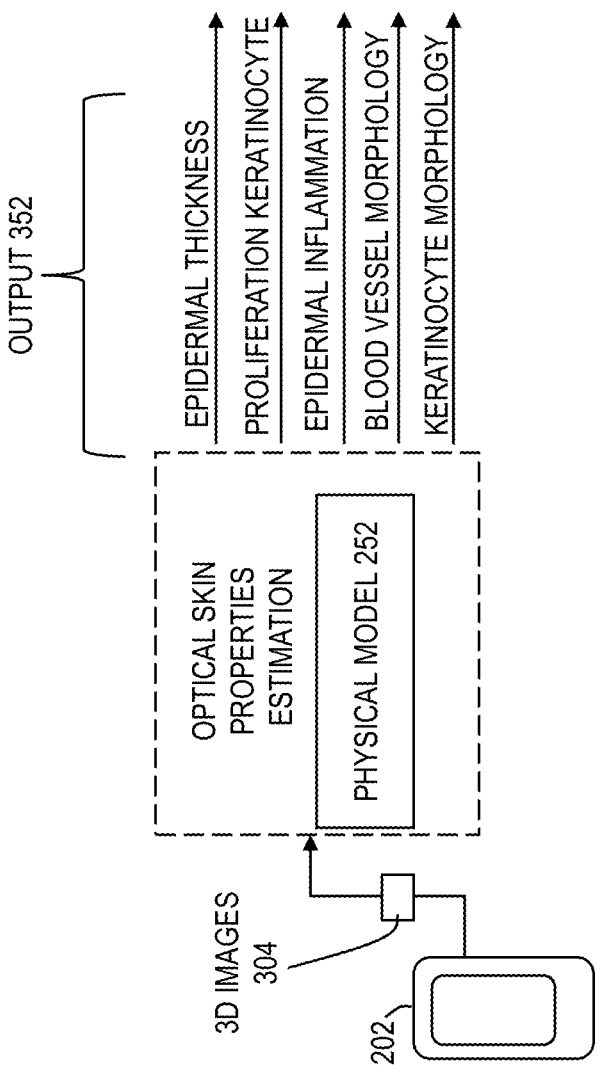
FIG. 3A is a block diagram of further details of a model in the system in accordance with one or more embodiments of the present invention.

FIG. 2 illustrates a block diagram of an example system 200 for automatic association between physical/inner skin properties and visual/surface skin properties to provide a comprehensive skin disorder severity assessment in accordance with one or more embodiments of the present invention. FIG. 3A illustrates a block diagram of further details of the model in system 200 utilized for skin disorder severity assessment in accordance with one or more embodiments of the present invention. FIG. 3B illustrates a block diagram of further details of the models in system 200 utilized for automatic association between physical/inner skin properties and visual/surface skin properties to provide a comprehensive skin disorder severity assessment in accordance with one or more embodiments of the present invention, where the skin disorder is psoriasis. FIG. 4 illustrates a flow diagram of a process 400 for automatically determining an association between physical/inner skin properties and visual/surface skin properties to provide a comprehensive skin disorder severity assessment in accordance with one or more embodiments of the present invention. An example of comprehensive skin disorder severity assessment can be a comprehensive psoriasis severity assessment although other skin disorders can be accessed. The process 400 is performed by system 200.

Hardware and software components, including but not limited to processors 101, system memory 103, ROM 104, RAM 105, software 111, mass storage 110, etc., discussed in computer system 100 of FIG. 1 can be respectively utilized in FIGS. 2, 3A, and 3B. For example, computer system 202 and computer system 230 can include the hardware and software components of computer system 100. Additionally, the computer system 202 and computer system 230 can include and/or be integrated with the components of FIGS. 7, 8, 9, and 10 discussed herein.

As seen in FIG. 2, the system 200 includes a computer system 202 which includes one of more software applications 210, a spectrometer module 212, and a camera 214. The camera 214 is configured to capture images, such as two-dimensional (2D) images, using red, green, blue colors. The spectrometer module 212 is configured to capture three-dimensional (3D) images using different wavelengths of light to penetrate the skin. The computer system 202 can be a mobile device such as a spectrometer smartphone, mobile phone, laptop, tablet, gaming system, etc., having camera capabilities and spectrometer capabilities.

The spectrometer module 212 can be a highly sensitive mobile phone based spectrometer that captures 3D images in a rapid, non-invasive manner. An example low cost spectrometer can utilize the camera of the mobile phone to image the field after moving through a diffraction grating while using the mobile phone image sensors and built in optical elements. Another example spectrometer can have an integrated grating and sensor which are compact, accurate, and calibrated, where resolutions of about 10 nanometers (nm) can be achieved. Additionally, ultraviolet (UV) and visible light emitting diode (LED) excitation sources are built into the device. In some examples, data collection and analysis can be simplified using wireless interfaces and logical control on the smart phone. In some cases, by utilizing an external sensor, the mobile phone camera can be used in conjunction with spectral measurements. In general, reflectance confocal microscopy (RCM) can be utilized in the spectrometer module 212 to generate the 3D images. Spectrally encoded confocal microscopy (SECM) is a RCM technology that uses a diffraction grating and broadband light source to spread illumination light over a line on the skin (e.g., tissue) and conduct line confocal imaging without using a beam scanning device. Further, the slit SECM approach uses low-cost optical elements, an inexpensive LED as the light source, and a two-dimensional imaging sensor to acquire confocal images. Complementary metal-oxide-semiconductor (CMOS) imaging sensors in smartphones have a large number of pixels and high sensitivity, and these imaging sensors can be used as the imaging sensor in the slit SECM approach, thereby providing the smartphone confocal microscope.

The computer system 202 can include a physical skin properties deep learning model 252, a visual skin properties deep learning model 254, and a skin disorder severity assessment deep learning model 256 for automatically determining an association between physical skin properties and visual skin properties to provide a comprehensive skin disorder severity assessment. In one or more embodiments of the invention, the skin disorder severity assessment deep learning model 256 can be a psoriasis severity assessment deep learning model for automatically determining an association between physical skin properties and visual skin properties to provide a comprehensive psoriasis severity assessment. In one or more embodiments of the invention, a computer system 230 can additionally and/or alternatively include the physical/inner skin properties deep learning model 252, visual/surface skin properties deep learning model 254, and the skin disorder severity assessment deep learning model 256, such that some or part of the processing can be offloaded or distributed. The computer system 230 includes one or more software applications 240 for operating as discussed herein.

FIG. 3A shows that 3D images 304 can be utilized as input by the physical skin properties deep learning model 252 to provide an optical skin properties estimation. Particularly, the physical skin properties deep learning model 252 can provide an output 352 of epidermal thickness, epidermal inflammation, vessel morphology, keratinocyte morphology, and proliferation of keratinocytes, which can be used to diagnose skin disorders. FIG. 3B illustrates how a combination of 3D images 304 and 2D images 302 can be utilized for automatic association between physical/inner skin properties and visual/surface skin properties to provide a comprehensive psoriasis skin disorder severity assessment in accordance with one or more embodiments of the present invention. Currently, there are no biomarkers for disease activity in psoriasis, so the current practice for assessing and recording the severity of psoriasis is called "Psoriasis Area Severity Index" (PAST). PASI requires measuring four parameters which are erythema, scales, area, and induration, for four different body regions by visual inspection. Not only is PASI scoring impractical for daily clinics, but even experienced dermatologists show high variations when subjectively measuring the severity of psoriasis. Psoriasis has other relevant clinical parameters that may be assessed objectively including epidermal thickness, proliferation of keratinocytes, epidermal inflammation, blood vessel morphology, and keratinocyte morphology, and one or more embodiments take these additional parameters into account as physical/inner skin parameters.

The process 400 shown in FIG. 4 will now be described with reference to FIG. 4 and the corresponding elements of system 200 (shown in FIGS. 2 and 3B) that perform process 400. At block 402 of the process 400, the computer system 202 is configured capture 2D images 302 (e.g., also referred to as a RGB images) of one or more areas of a person using the camera 214 and capture a 3D images 304 (e.g., also referred to as a 3D conical depth images) of one or more areas of the person using the spectrometer module 212. The 2D image and 3D image are representative of the same area or areas of the person. The person can take images of himself or herself, or another user can capture the images of the person using the computer system 202. RGB skin surface images (i.e., 2D images) are for measuring visual/surface skin parameters including erythema, scales, and lesion area. The 3D focal depth images are for measuring physical/inner layers skin parameters including epidermal thickness, epidermal inflammation, vessel morphology, keratinocyte morphology, and proliferation of keratinocytes.

Figure 5A:
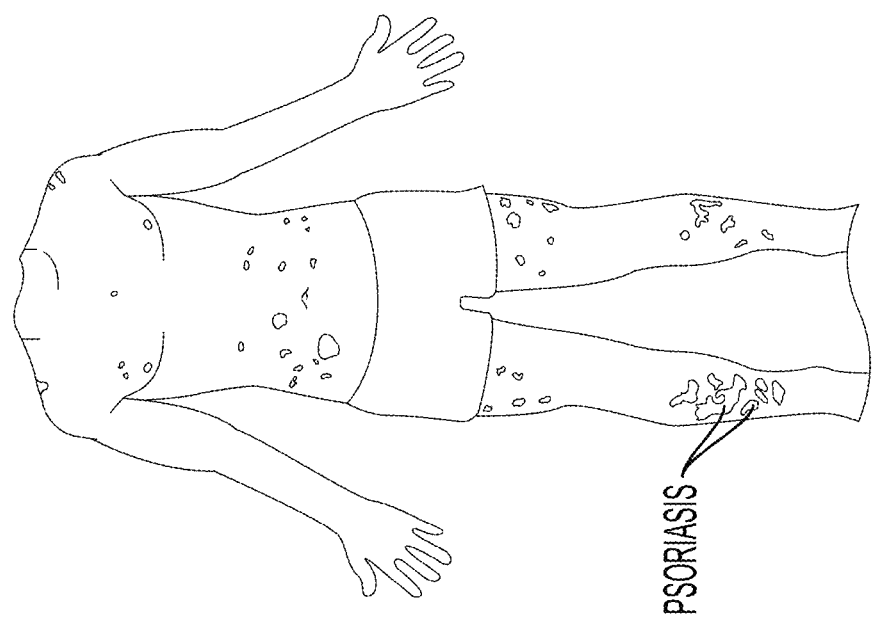
FIG. 5A illustrates an example two-dimensional (2D) image of skin according to one or more embodiments of the invention.

FIG. 5A illustrates an example 2D image, which is an RGB image, of psoriatic skin according to embodiments of the invention. FIG. 5A shows a person with psoriasis but does not show the physical/inner layer underneath the surface of the skin. RGB images provide 2D images for each of red, green, and blue channels (i.e., 3 channels) resulting in an image with width*height*3, where the asterisk * denotes multiplication. The RGB image camera cannot penetrate the skin of the person, and the RGB image only reflects the skin surface absorption of light for the 3 mentioned channels.

FIG. 5B illustrates an example of 3D imaging of (normal) human skin according to embodiments of the invention. View 510 represents a cross-sectional view of a person's skin. The 3D skin imaging is used to capture multiple (e.g., 5) horizontal images 502A, 502B, 502C, 502D, 502E for different inner skin layers of the person at different depths via the spectrometer module 212. The horizontal section of images are depicted along the x and y axes. Horizontal image 502A is the upper most layer (which could include the outer most (surface) layer of the skin) while horizontal image 502E is the inner most layer of the person's skin, while the other horizontal images 502B, 502C, 502D are respectively in between. Each horizontal image 502A, 502B, 502C, 502D, 502E represents the reflection of the light source via the spectrometer module 212 at a specific and different wavelength of light. Stacking all horizontal images (which are 2D images) captured at different wavelengths, which correspond to different locations on the z-axis, results in a 3D cube of image data or stack 520 having width * height * depth where depth represents the number of different wavelengths provided by the 3D imaging device (i.e., the spectrometer module 212). Accordingly, each stack 520 captured by the spectrometer module 212 represents the 3D image 304. The software application 210 includes and/or communicates with image processing software to process the horizontal images into the stack 520 in accordance with embodiments of the invention.

Returning to the process 400 in FIG. 4, at block 404, the software application 210 of computer system 202 can receive the 2D images 302 and 3D images 304, and can transfer the 2D image 302 to the visual/surface skin properties deep learning model 254 and 3D image 304 to the physical/inner skin properties deep learning model 252. As noted above, the computer system 202 and/or computer system 230 can include the physical/inner skin properties deep learning model 252, the visual/surface skin properties deep learning model 254, and the skin disorder severity assessment deep learning model 256. In one or more embodiments of the invention, the software application 210 can transfer the 2D images 302 and 3D images 304 to the computer system 230, and can cause/instruct the software application 240 to process the 2D images 302 and 3D images 304 using the visual skin properties deep learning model 254, the physical skin properties deep learning model 252, and (later) the skin disorder severity assessment deep learning model 256 as discussed herein. Accordingly, processing using the physical skin properties deep learning model 252, the visual skin properties deep learning model 254, and the skin disorder severity assessment deep learning model 256 can be partly and/or entirely by computer system 202 and/or computer system 230.

The physical skin properties deep learning model 252 is configured to measure physical/inner skin properties as obtained/determined vessel morphology and keratinocyte morphology using focal depth images, which are 3D images 304. The physical skin properties deep learning model 252 is configured to provide output 352. For training the physical skin properties deep learning model 252, the input is 3D focal depth images and the output 352 has five values as physical skin measures, which include a value for epidermal thickness, proliferation of keratinocytes, epidermal inflammation, blood vessel morphology, and keratinocyte morphology. Epidermal thickness measure is a scalar value between 0-1 which refers to the epidermal thickness in millimeter (mm). For example, epidermal thickness for normal skin is approximately 0.1 mm while this value is greater for skin disorders. Proliferation of keratinocytes and epidermal inflammation are also scalar values between 0-1 which refer to the growth and inflammation factors respectively. These values are greater for skin disorders than normal skin. Blood vessel and keratinocyte morphology are binary values where 0 means normal and 1 means abnormal. For example, psoriasis can show changes in the size, amount, diameter, and three-dimensional structure of their blood vessels and keratinocyte.

The visual skin properties deep learning model 254 is configured for measuring visual skin properties using RGB images, which are 2D images 302. For training visual skin properties deep learning model 254, the input is 2D images (RGB images) and the output 354 has three values as visual skin measures: amount of redness (i.e., erythema severity score, e.g., from 0 to 4), amount of scales (i.e., scale severity score, e.g., from 0 to 4), and lesion area (i.e., area severity score, e.g., from 0 to 6). The output 354 of visual skin properties deep learning model 254 represents PASI scoring. Lesion area is the percent of affected skin area with respect to the total skin area. In other words, lesion area can be calculated by dividing the total number of pixels inside the lesion by the total number of skin pixels. The estimated percent can be transformed into a grade from 0 to 6: grade [0] denotes 0% of involved area, grade [1] denotes <10% of involved area, grade [2] denotes 10-29% of involved area, grade [3] denotes 30-49% of involved area, grade [4] denotes 50-69% of involved area, grade [5] denotes 70-89% of involved area, grade [6] denotes 90-100% of involved area.

Deep learning is a type of machine learning technique that can be used to classify 1D features, 2D images and/or 3D images by automatically learning and extracting the image features that are important for classification. A basic architecture for a deep learning network includes an input layer, N convolutional layers, and output layers. In the training phase, given a large dataset of input and output pairs, a deep learning algorithm operates to find the optimal set of weights that minimizes the difference between its prediction and expected output. In other words, it learns the associations between a set of inputs and outputs. During the testing phase, the deep learning model feeds an input image to the learned model (with the adjusted weights) to extract the corresponding output labels. With transfer learning, instead of starting the deep learning process from scratch, one or more embodiments can import a pre-trained model that could have been trained on a different dataset to solve a different problem. The weights of the last few or all layers can be adjusted during training to fit the new task. Further regarding deep learning is discussed in FIGS. 6, 7, 8, 9, and 10.

Continuing the process 400 of FIG. 4, at block 406, the software application 210 of computer system 202 can provide (and/or software application 210 can cause/instruct the software application 240 of computer system 230 to provide) the output 352 and output 354 as input to the skin disorder severity assessment deep learning model 256. The skin disorder severity assessment deep learning model 256 is a deep learning model on top of the two sub-models, which learns the association between physical/inner skin measurements and visual/surface skin measurements for accurate skin disorder severity assessment, for example, such as psoriasis severity assessment. For training skin disorder severity assessment deep learning model 256 and during operation, the input includes eight values (physical/inner skin measures output 352 and visual skin measures output 354), and after processing by the skin disorder severity assessment deep learning model 256, the skin disorder severity assessment deep learning model 256 is configured to provide output 356 which includes a selection from psoriasis severity labels (i.e., normal, mild, moderate, severe, and/or very severe), along with the contribution of the five physical skin properties (i.e., output 352) and three visual skin properties (i.e., output 354) to the network decision of the output 356, at block 408. The severity output will be a binary vector of length equal to the number of severity labels, which is 5 in the example case of psoriasis. For example, if the severity output is [0,1,0,0,0], this means the severity label is "mild". The contribution results will be a vector of two values which refer to the contribution of the set of physical and visual skin properties, respectively. For instance, if the contribution output is [0.8,0.2], this means 80% of the model's decision is determined from the physical skin measurements while 20% is determined from the visual skin measurements. Subsequently, the computer system 202 can associate output 356 with one or more types of suggested treatment plans and/or medications respectively for normal healthy skin, mild psoriasis, moderate psoriasis, severe psoriasis, and/or very severe psoriasis, thereby providing a diagnosis for the patient.

Figure 6:
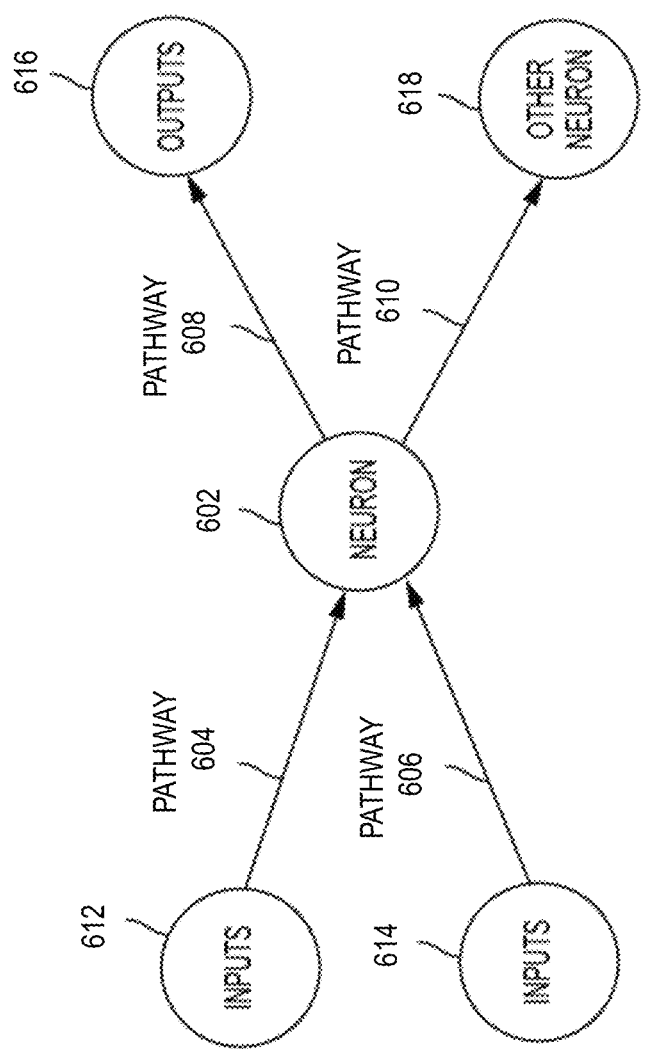
FIG. 6 illustrates a simplified diagram of input and output connections of a biological neuron.

Further regarding deep learning models is provided. A general description of how a typical artificial neural networks (ANN) operates will now be provided with reference to FIGS. 6, 7, and 8. A typical ANN models the human brain, which includes about one hundred billion interconnected cells called neurons. FIG. 6 depicts a simplified diagram of a biological neuron 602 having pathways 604, 606, 608, 610 that connect it to upstream inputs 612, 614, downstream outputs 616 and downstream "other" neurons 618, configured and arranged as shown. Each biological neuron 602 sends and receives electrical impulses through pathways 604, 606, 608, 610. The nature of these electrical impulses and how they are processed in biological neuron 602 are primarily responsible for overall brain functionality. The pathway connections between biological neurons can be strong or weak. When a given neuron receives input impulses, the neuron processes the input according to the neuron's function and sends the result of the function to downstream outputs and/or downstream "other" neurons.

Figure 7:
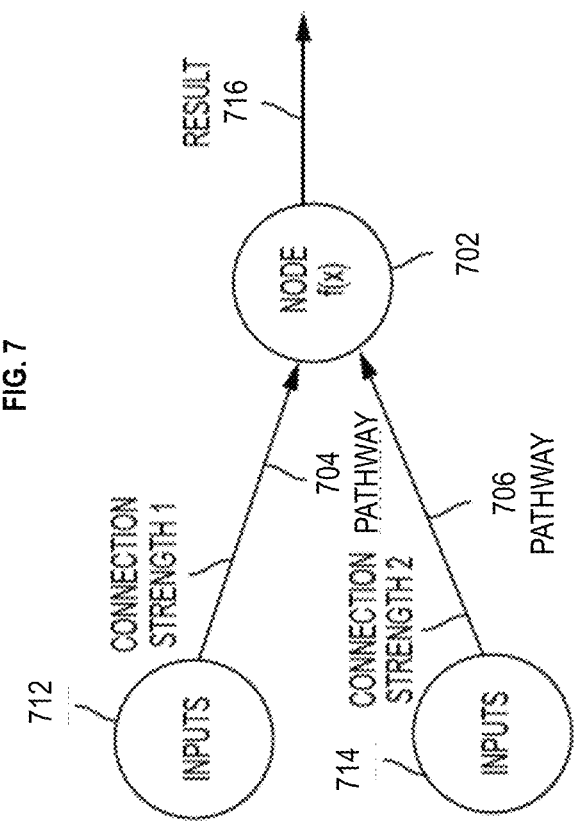
FIG. 7 illustrates a known simplified model of the biological neuron shown in FIG. 6.

Biological neuron 602 is modeled in FIG. 7 as a node 702 having a mathematical function f(x), depicted by the equation shown in FIG. 7. Node 702 takes electrical signals from inputs 712, 714, multiplies each input 712, 714 by the strength of its respective connection pathway 704, 706, takes a sum of the inputs, passes the sum through a function, f(x), and generates a result 716, which can be a final output or an input to another node, or both. In the present description, an asterisk (*) is used to represent a multiplication. Weak input signals are multiplied by a very small connection strength number, so the impact of a weak input signal on the function is very low. Similarly, strong input signals are multiplied by a higher connection strength number, so the impact of a strong input signal on the function is larger. The function f(x) is a design choice, and a variety of functions can be used. An example design choice for f(x) is the hyperbolic tangent function, which takes the function of the previous sum and outputs a number between minus one and plus one.

Figure 8:
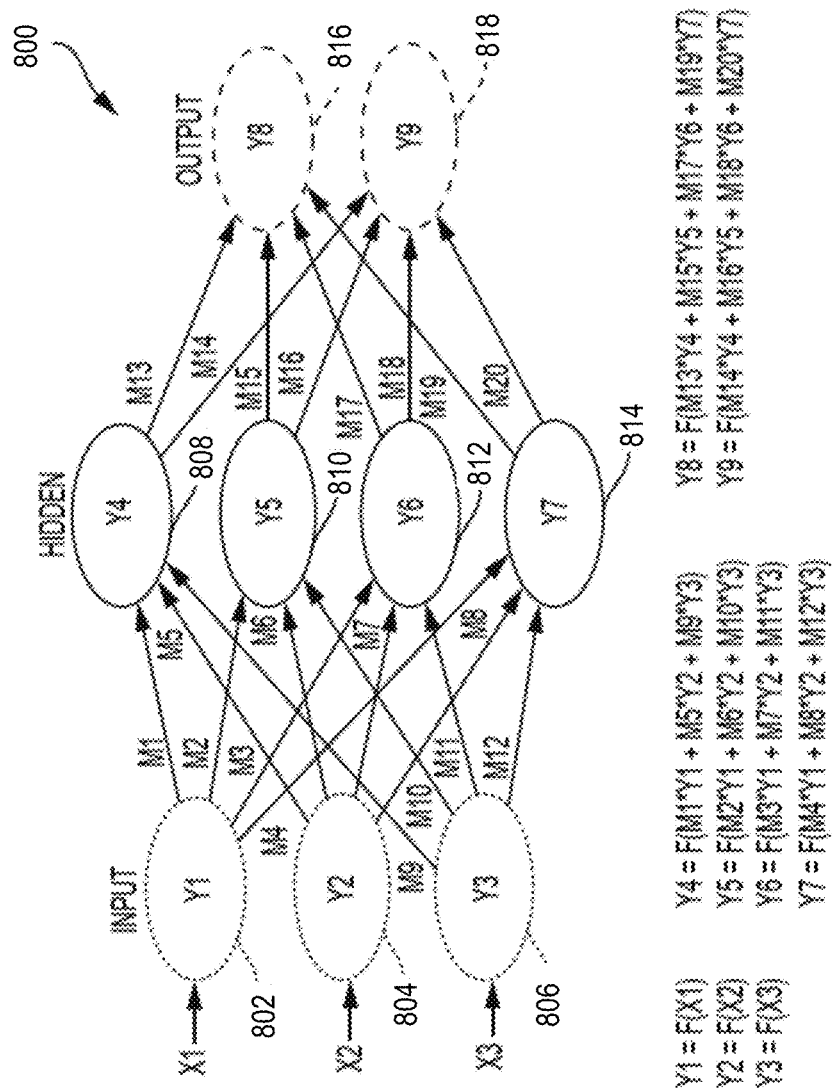
FIG. 8 illustrates a known simplified model of an artificial neural network (ANN) incorporating the biological neuron model shown in FIG. 7.

FIG. 8 depicts a simplified ANN model 800 organized as a weighted directional graph, wherein the artificial neurons are nodes (e.g., 802, 808, 816), and wherein weighted directed edges (e.g., m1 to m20) connect the nodes. It should be noted that the ANN model 800 depicted is a fully connected deep neural network (DNN); however, the technical solutions described herein are also applicable in with other types of ANNs, such as convolutional neural network (CNN), partially connected DNN, and the like, and not just limited to a fully connected DNN. ANN model 800 is organized such that nodes 802, 804, 806 are input layer nodes, nodes 808, 810, 812, 814 are hidden layer nodes and nodes 816, 818 are output layer nodes. Each node is connected to every node in the adjacent layer by connection pathways, which are depicted in FIG. 8 as directional arrows having connection strengths m1 to m20. Although only one input layer, one hidden layer, and one output layer are shown, in practice, multiple input layers, hidden layers, and output layers can be provided.

Similar to the functionality of a human brain, each input layer node 802, 804, 806 of ANN 800 receives inputs x1, x2, x3 directly from a source (not shown) with no connection strength adjustments and no node summations. Accordingly, y1=f(x1), y2=f(x2) and y3=f(x3), as shown by the equations listed at the bottom of FIG. 8. Each hidden layer node 808, 810, 812, 814 receives its inputs from all input layer nodes 802, 804, 806 according to the connection strengths associated with the relevant connection pathways. Thus, in hidden layer node 808, y4=f(m1*y1+m5*y2+m9*y3), wherein * represents a multiplication. A similar connection strength multiplication and node summation is performed for hidden layer nodes 810, 812, 814 and output layer nodes 816, 818, as shown by the equations defining functions y5 to y9 depicted at the bottom of FIG. 8.

ANN model 800 processes data records one at a time, and it "learns" by comparing an initially arbitrary classification of the record with the known actual classification of the record. Using a training methodology knows as "backpropagation" (i.e., "backward propagation of errors"), the errors from the initial classification of the first record are fed back into the network and used to modify the network's weighted connections the second time around, and this feedback process continues for many iterations. In the training phase of an ANN, the correct classification for each record is known, and the output nodes can therefore be assigned "correct" values. For example, a node value of "1" (or 0.9) for the node corresponding to the correct class, and a node value of "0" (or 0.1) for the others. It is thus possible to compare the network's calculated values for the output nodes to these "correct" values, and to calculate an error term for each node (i.e., the "delta" rule). These error terms are then used to adjust the weights in the hidden layers so that in the next iteration the output values will be closer to the "correct" values.

There are many types of neural networks, but the two broadest categories are feed-forward and feedback/recurrent networks. ANN model 800 is a non-recurrent feed-forward network having inputs, outputs and hidden layers. The signals can only travel in one direction. Input data is passed onto a layer of processing elements that perform calculations. Each processing element makes its computation based upon a weighted sum of its inputs. The new calculated values then become the new input values that feed the next layer. This process continues until it has gone through all the layers and determined the output. A threshold transfer function is sometimes used to quantify the output of a neuron in the output layer.

A feedback/recurrent network includes feedback paths, which mean that the signals can travel in both directions using loops. All possible connections between nodes are allowed. Because loops are present in this type of network, under certain operations, it can become a non-linear dynamical system that changes continuously until it reaches a state of equilibrium. Feedback networks are often used in associative memories and optimization problems, wherein the network looks for the best arrangement of interconnected factors.

The speed and efficiency of machine learning in feed-forward and recurrent ANN architectures depend on how effectively the cross-point devices of the ANN cross-bar array perform the core operations of typical machine learning algorithms. Although a precise definition of machine learning is difficult to formulate, a learning process in the ANN context can be viewed as the problem of updating the cross-point device connection weights so that a network can efficiently perform a specific task. The cross-point devices typically learn the necessary connection weights from available training patterns. Performance is improved over time by iteratively updating the weights in the network. Instead of following a set of rules specified by human experts, ANNs "learn" underlying rules (like input-output relationships) from the given collection of representative examples. Accordingly, a learning algorithm can be generally defined as the procedure by which learning rules are used to update and/or adjust the relevant weights.

The three main learning algorithm paradigms are supervised, unsupervised and hybrid. In supervised learning, or learning with a "teacher," the network is provided with a correct answer (output) for every input pattern. Weights are determined to allow the network to produce answers as close as possible to the known correct answers. Reinforcement learning is a variant of supervised learning in which the network is provided with only a critique on the correctness of network outputs, not the correct answers themselves. In contrast, unsupervised learning, or learning without a teacher, does not require a correct answer associated with each input pattern in the training data set. It explores the underlying structure in the data, or correlations between patterns in the data, and organizes patterns into categories from these correlations. Hybrid learning combines supervised and unsupervised learning. Parts of the weights are usually determined through supervised learning, while the others are obtained through unsupervised learning.

As previously noted herein, in order to limit power consumption, the cross-point devices of ANN chip architectures (or models) are often designed to utilize offline learning techniques, wherein the approximation of the target function does not change once the initial training phase has been resolved. Offline learning allows the cross-point devices of cross-bar-type ANN architectures to be simplified such that they draw very little power.

Figure 9:
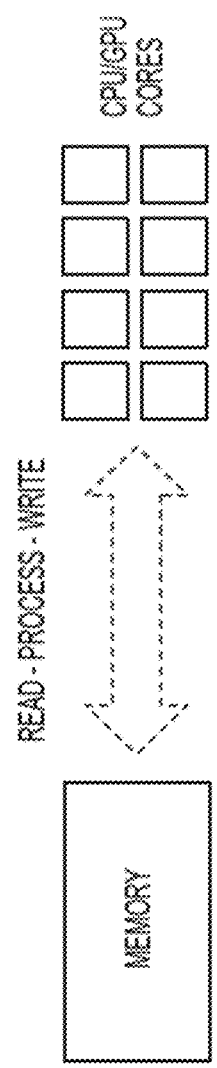
FIG. 9 illustrates a simplified illustration of a typical read-process-write weight update operation.

Notwithstanding the potential for lower power consumption, executing offline training can be difficult and resource intensive because it is typically necessary during training to modify a significant number of adjustable parameters (e.g., weights) in the ANN model to match the input-output pairs for the training data. FIG. 9 depicts a simplified illustration of a typical read-process-write weight update operation, wherein CPU/GPU cores (i.e., simulated "neurons") read a memory (i.e., a simulated "synapse") and perform weight update processing operations, then write the updated weights back to memory. Accordingly, simplifying the cross-point devices of ANN architectures to prioritize power-saving, offline learning techniques typically means that training speed and training efficiency are not optimized.

Figure 10:
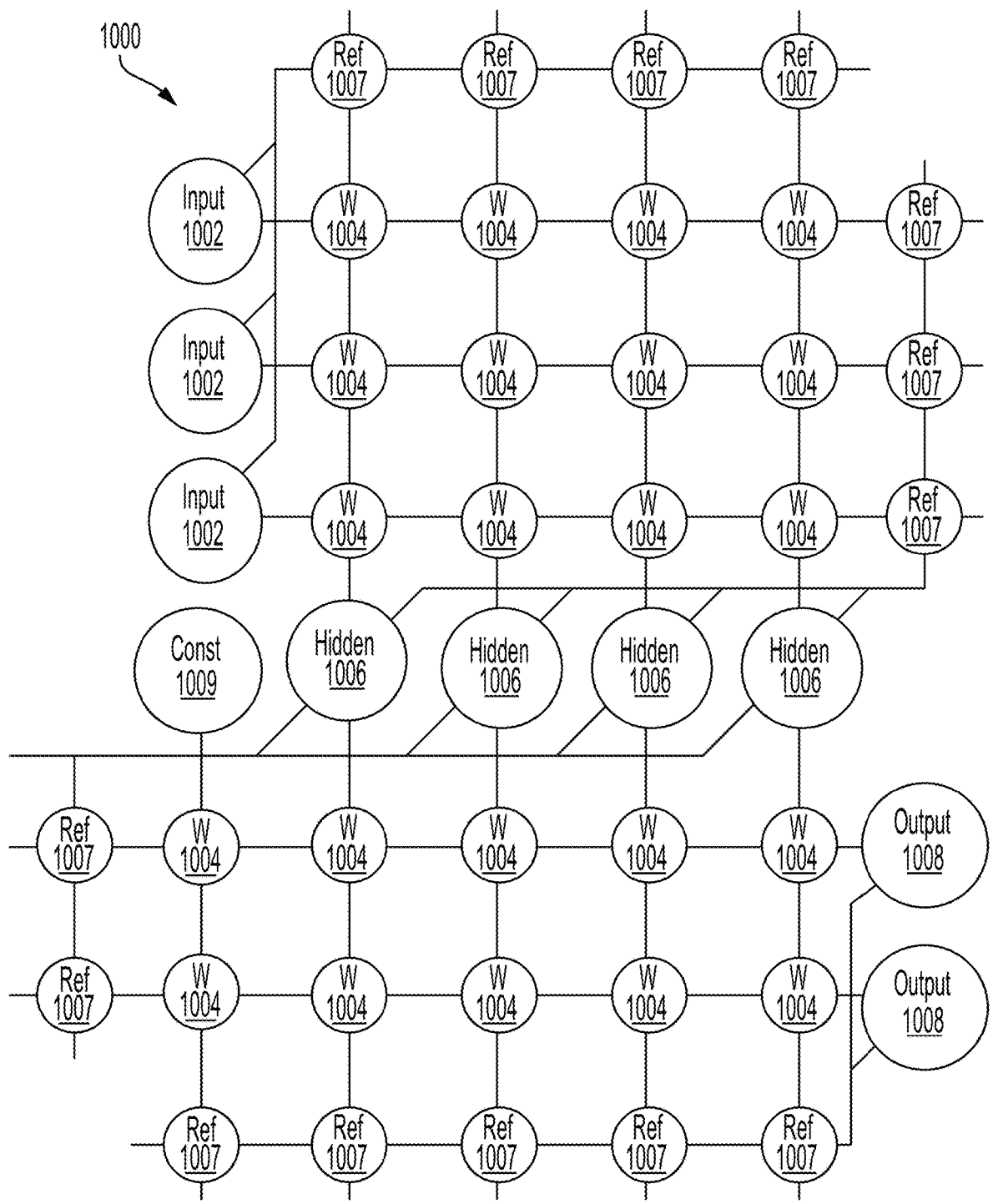
FIG. 10 illustrates an artificial neural network (ANN) architecture in accordance with one or more embodiments of the invention.

FIG. 10 illustrates an artificial neural network (ANN) architecture 1000. During feed-forward operation, a set of input neurons 1002 each provide an input voltage in parallel to a respective row of weights 1004. A weight 1004 is a cross-point device, such as a resistive processing unit (RPU). The weights 1004 each have a settable resistance value, such that a current output flows from the weight 1004 to a respective hidden neuron 1006 to represent the weighted input. The current output (I) by a given weight is determined as I=v/r, where V is the input voltage from the input neuron 1002 and r is the set resistance of the weight 1004. The current from each weight adds column-wise and flows to a hidden neuron 1006. A set of reference weights 1007 have a fixed resistance and combine their outputs into a reference current that is provided to each of the hidden neurons 1006. Because conductance values can only be positive numbers, some reference conductance is needed to encode both positive and negative values in the matrix. The currents produced by the weights 1004 are continuously valued and positive, and therefore the reference weights 1007 are used to provide a reference current, above which currents are considered to have positive values and below which currents are considered to have negative values. By using high ion conductivity electrolyte layer between ion reservoir layers, one or more embodiments of the present invention facilitate very high speed (nanosecond to sub nanosecond) response speed.

The hidden neurons 1006 use the currents from the array of weights 1004 and the reference weights 1007 to perform some calculation. The hidden neurons 1006 then output a voltage of their own to another array of weights 1007. This array performs in the same way, with a column of weights 1004 receiving a voltage from their respective hidden neuron 1006 to produce a weighted current output that adds row-wise and is provided to the output neuron 1008.

It should be understood that any number of these stages can be implemented, by interposing additional layers of arrays and hidden neurons 1006. It should also be noted that some neurons can be constant neurons 1009, which provide a constant voltage to the array. The constant neurons 1009 can be present among the input neurons 1002 and/or hidden neurons 1006 and are only used during feed-forward operation.

During back propagation, the output neurons 1008 provide a voltage back across the array of weights 1004. The output layer compares the generated network response to training data and computes an error. The error is applied to the array as a voltage pulse, where the height and/or duration of the pulse is modulated proportional to the error value. In this example, a row of weights 1004 receives a voltage from a respective output neuron 1008 in parallel and converts that voltage into a current which adds column-wise to provide an input to hidden neurons 1006. The hidden neurons 1006 combine the weighted feedback signal with a derivative of its feed-forward calculation and stores an error value before outputting a feedback signal voltage to its respective column of weights 1004. This back propagation travels through the entire network 1000 until all hidden neurons 1006 and the input neurons 1002 have stored an error value.

During weight updates, the input neurons 1002 and hidden neurons 1006 apply a first weight update voltage forward and the output neurons 1008 and hidden neurons 1006 apply a second weight update voltage backward through the network 1000. The combinations of these voltages create a state change within each weight 1004, causing the weight 1004 to take on a new resistance value. In this manner, the weights 1004 can be trained to adapt the neural network 1000 to errors in its processing. It should be noted that the three modes of operation, feed forward, back propagation, and weight update, do not overlap with one another.

Figure 11:
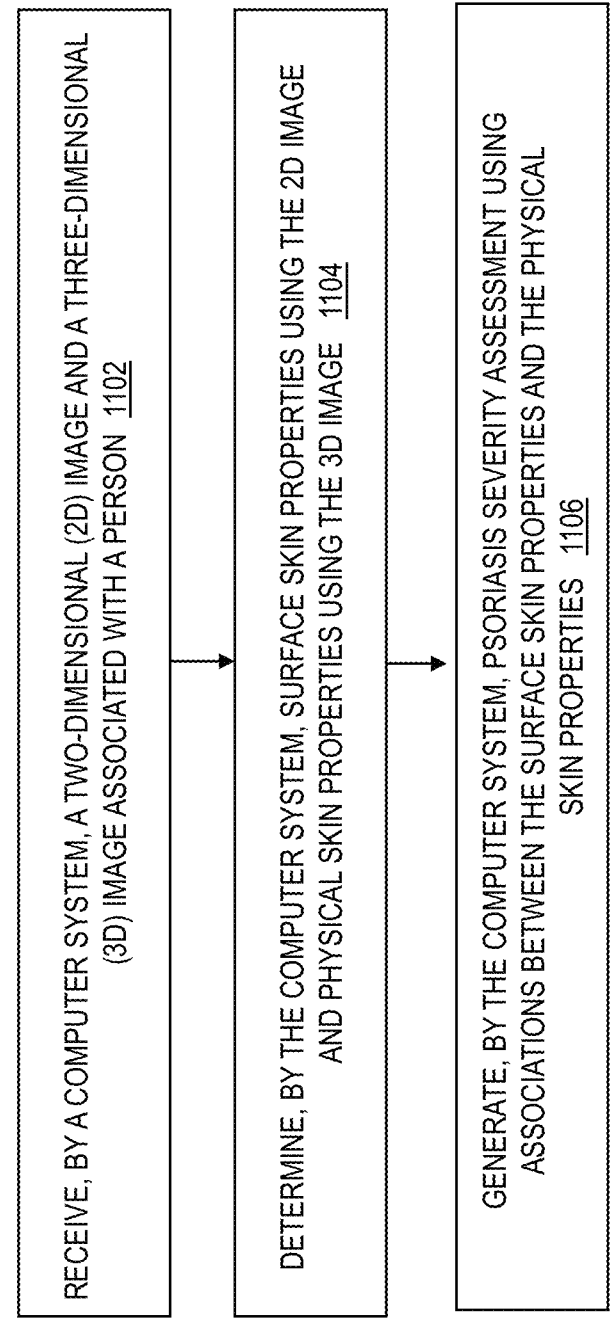
FIG. 11 is a flow diagram of a computer-implemented method for automatic association between physical/inner and visual/surface skin properties for comprehensive skin disorder severity assessment according to one or more embodiments of the invention.

FIG. 11 is a flow diagram of a computer-implemented method 1100 for automatic association between physical/inner properties and visual/surface skin properties for comprehensive skin disorder severity assessment, such as, for example, psoriasis severity assessment according to one or more embodiments of the invention. Reference can be made to FIGS. 1-10 discussed herein.

At block 1102, the computer system 202 and/or computer system 230 instructed by computer system 202 is configured to receive two-dimensional (2D) images (e.g., one or more 2D images 302) and three-dimensional (3D) images (e.g., one or more 3D images 304) associated with a person. At block 1104, the computer system 202 and/or computer system 230 instructed by computer system 202 is configured to determine surface skin properties (e.g., output 354) using the 2D images and physical skin properties (e.g., output 352) using the 3D images. At block 1106, the computer system 202 and/or computer system 230 instructed by computer system 202 is configured to generate psoriasis severity assessment (e.g., output 356) using associations between the surface skin properties (e.g., output 354) and the physical skin properties (e.g., output 352).

The 2D images represent a surface of skin of the person. The 3D images represent a composite or cube of inner layers (which can include the outer/surface layer) of skin of the person. Determining the surface skin properties using the 2D images include using a trained model (e.g., visual/surface skin properties deep learning model 254) to determine the surface skin properties from the 2D images. The surface skin properties include a redness severity score, a scale severity score, and an area severity score (e.g., output 354).

Determining the physical skin properties using the 3D images include using a trained model (e.g., physical/inner skin properties deep learning model 252) to determine the physical skin properties. The physical skin properties include an epidermal thickness value, a proliferation of keratinocytes value, an epidermal inflammation value, a blood vessel morphology value, and a keratinocyte morphology value (e.g., output 352).

A trained model (e.g., skin disorder severity assessment deep learning model 256) is used to determine the associations and to generate the psoriasis severity assessment using the associations between the surface skin properties and the physical skin properties. The psoriasis severity assessment includes a selection from psoriasis severity labels (e.g., normal healthy skin, mild psoriasis, moderate psoriasis, severe psoriasis, and/or very severe psoriasis).

Now turning to one or more embodiments of the invention, automatic measurement of PASI scoring using structured lights is provided. The current practice of assessing and recording the severity of psoriasis is called "Psoriasis Area Severity Index" (PAST), as noted herein. The body is divided into four sections which are the head (H) representing about 10% of a person's skin, arms (A) representing about 20%, the trunk (T) representing about 30%, and legs (L) representing about 40%. Each of these areas (i.e., head, arms, trunk, legs) is scored by itself, and then the four scores are combined into the final PASI score. Within each area (i.e., head, arms, trunk, legs), the severity is estimated by three clinical signs: erythema (redness), induration (thickness), and desquamation (scaling) in addition to lesion area. Severity parameters are measured on a scale of 0 to 4, from none being 0 to maximum being 4.

Although severity scoring of some clinical signs (e.g., erythema) has been attempted using image analytics of RGB images with certain limitations, none of the attempted RGB techniques can compute severity of all required clinical signs using traditional RGB image analytics without a stereovision system for body capturing. A stereovision system employs more than one digital camera to capture body images from different perspectives. The mapping of the captured images results in RGB skin image as well as depth image. Because the relationship between the cameras are known, triangulation can be used to recover depth information. The cameras of the stereo system should be installed in a place with specific illumination conditions to allow for accurate measurements, which is usually installed in the clinic. However, such stereovision systems are bulky and expensive and require patients to visit the clinics.

One or more embodiments of the invention provide computer guided PASI measurements using a smartphone for remote and home based solutions to support remote disease management. One or more embodiments provide a system and method that allows any patient to estimate a PASI score remotely using his or her mobile phone and device/attachment.

Figure 12:
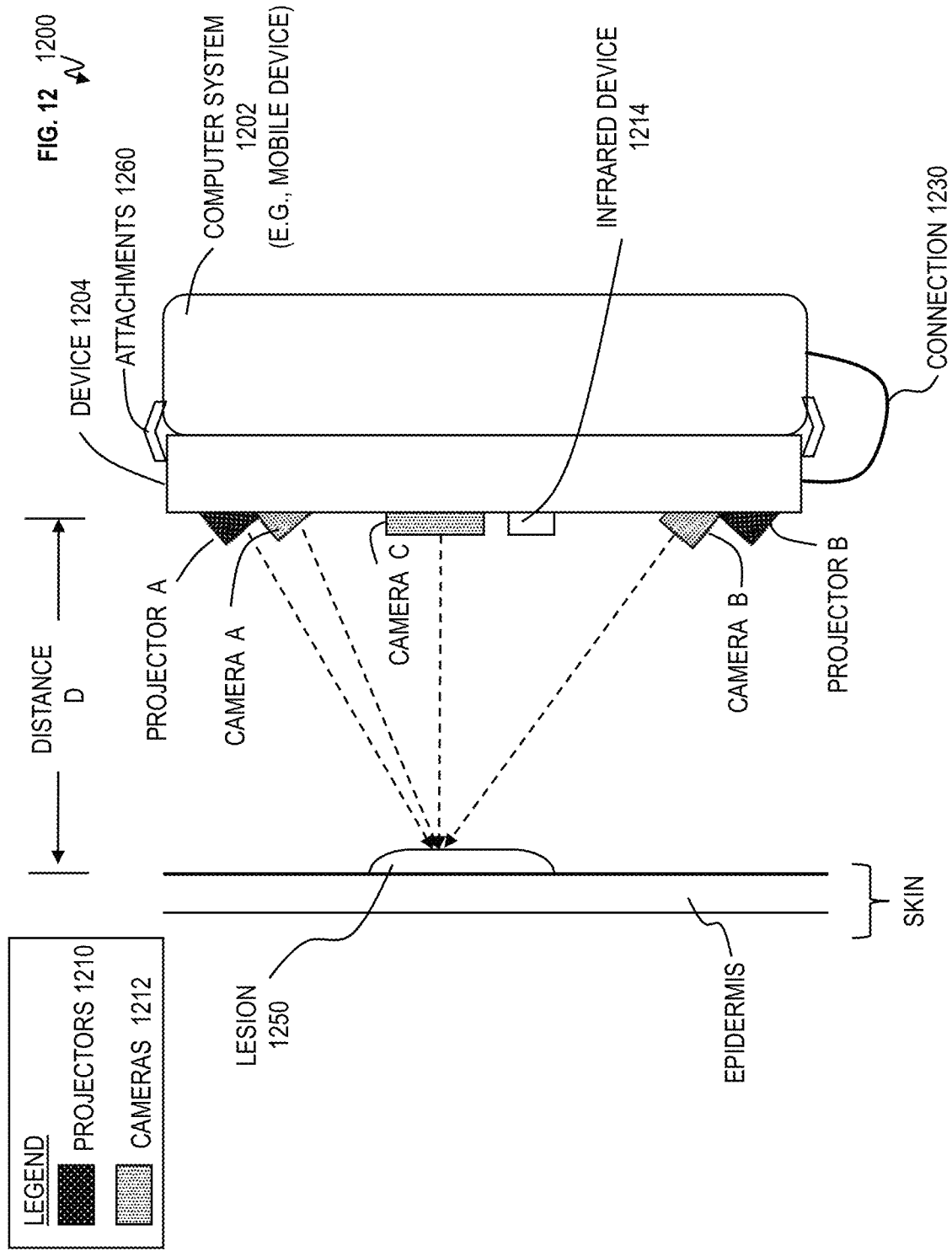
FIG. 12 is a block diagram of an example system for automatic measurement of skin disorder scoring using structured light in accordance with one or more embodiments of the invention.
Figure 13:
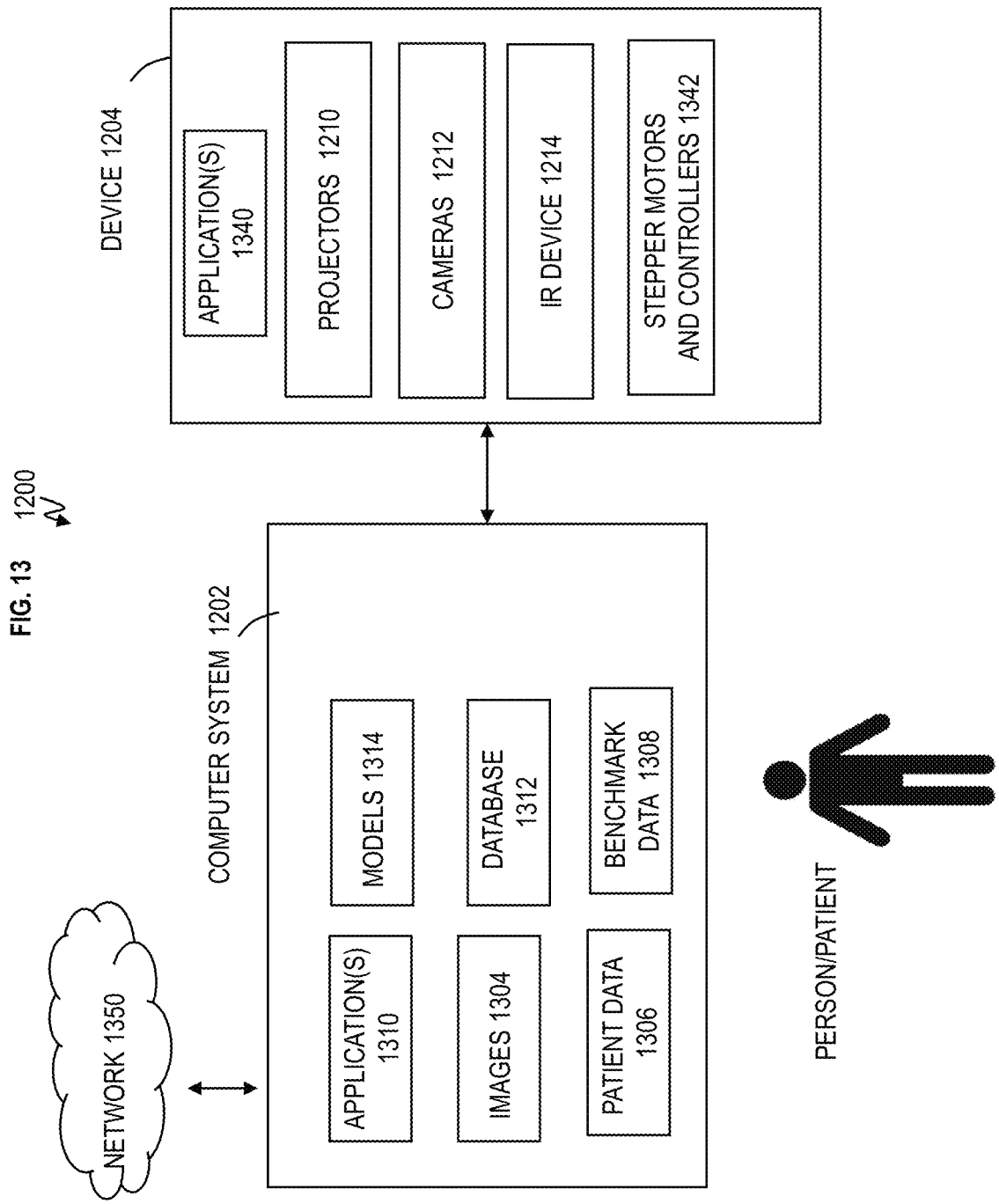
FIG. 13 is a block diagram of further details of the system in FIG. 12 in accordance with one or more embodiments of the present invention.

Turning now to FIG. 12, a block diagram is provided of an example system 1200 for automatic measurement of PASI scoring using structured lights in accordance with one or more embodiments of the present invention. FIG. 13 illustrates a block diagram of further details of the system 1200 in accordance with one or more embodiments of the present invention. The system 1200 is configured to use structured lights to automatically measure the all four required clinical parameters for PASI score, namely lesion area, erythema, thickness, and scaling, which existing RGB image analysis cannot measure.

Hardware and software components, including but not limited to processors 101, system memory 103, ROM 104, RAM 105, software 111, mass storage 110, etc., discussed in computer system 100 of FIG. 1 can be respectively utilized in FIGS. 12 and 13. For example, computer system 1202 and device 1204 can include the hardware and software components of computer system 100. Additionally, the computer system 1202 can be integrated with and/or include components of device 1204, computer system 202, and/or computer system 230.

FIG. 12 illustrates a computer system 1202, such as a mobile device which can be a smartphone (i.e., cell phone), laptop, tablet, gaming system, etc., communicatively coupled to device 1204 via one or more connections 1230. The connections 1230 can be a cord/cable such as USB cable connected to USB ports. The connections 1230 can represent a wireless connection such as a Bluetooth connection or another radio communication link. The computer system 1202 can also be physically attached to the device 1204 via one or more attachments 1260 such as fasteners, clamps, cases, etc., that can hold both the computer system 1202 and device 1204.

The device 1204 includes a structured light system which is configured to generate and capture structured light. Structured light is light having a known pattern, including, for example, lines, grids, bars, and the like. Structured light is used in so-called structured lighting processes to create 3D objects and measure distances in an observed scene. In an example structured lighting process, structured light having a known light pattern (e.g., grids and/or horizontal bars) is projected on to a scene. The structured light will deform when striking surfaces, which allows a vision system (e.g., a camera) to capture the deformed structured light and calculate therefrom depth and surface information of objects that have been struck by the structured light.

Structured lights have been used to capture micro 3D structures of the skin with fine details. Structured light systems work in a similar way to stereovision systems; however, one camera is replaced with a projector. To overcome the issue of relying on the texture variation in the object being scanned, the projector can project its own special textures, or patterns, (i.e., structured light) onto the object. These patterns, called structured encodings (i.e., structured lights) as they essentially encode the surface of the object being captured, can then be utilized within the frames captured by the system's camera. Because the relationship between the projector and camera is known, triangulation can be used to recover depth information.

Using 3D structured light technology, the device 1204 can approximate 3D properties such as, for example, the thickness of a lesion once the system 1200 identifies the lesion area on the skin. Using structured lights, the system 1200 determines the lesion area along with erythema and scaling. The system 1200 uses this information to compute a PASI score in an automatic manner even when the patient is remotely located from a doctor, such as a dermatologist. The system 1200 can be utilized to monitor disease progression without visiting the clinic.

The device 1204 includes light projectors 1210 designed to project/emit structured lights at desired colors and cameras 1212 capable of capturing images of a person's skin from different angles simultaneously with the different light patterns of the structured lights. When structured lights are projected from one light projector 1210, multiple images are simultaneously captured from different angles by the different cameras 1212. Although two light projectors 1210 are shown as projectors A and B, more or fewer than two light projectors can be utilized on the device 1204. Although three cameras 1212 are shown as cameras A, B, and C, more or fewer than three cameras can be utilized on the device 1204. The device 1204 can include an infrared (IR) device 1214 which can be utilized to measure the distance of the system 1200 (e.g., the device 1204 and computer system 1202) from the person (i.e., the person's skin). The device 1204 emits IR light (e.g., using a diode) and measures reflected light using a sensor. One of more software applications 1340 of device 1204 and/or software application 1310 of computer system 1202 can be used to measure the distance between the person and device 1204 based on the time from emitting the IR light to receiving the reflected IR light.

As noted above, the device 1204 is a scanning system that performs 3D scanning in which the device projects different light patterns, or structures, and captures the light as it returns to the cameras 1212. One or more software applications 1310 of computer system 1202 and/or one or more software applications 1340 of device 1204 then uses the information (i.e., captured images 1304) about how the patterns appear after being distorted by the skin (including the lesion area 1250 and non-lesion area (i.e., normal skin) to eventually recover the 3D geometry of the skin including both the lesion area 1250 and non-lesion area immediately around the lesion area 1250. Software applications 1310 and software applications 1340 include image processing software and/or communicate with image processing software in computer system 1202 to process images as discussed herein. The device 1204 can include stepper motors and controllers 1342. The stepper motors can move the light projectors 1210 to different angles for projecting the structured lights across the skin thereby providing the scanning, and the controllers control the color of light to be projected along with the scanning by the stepper motors.

Figure 14:
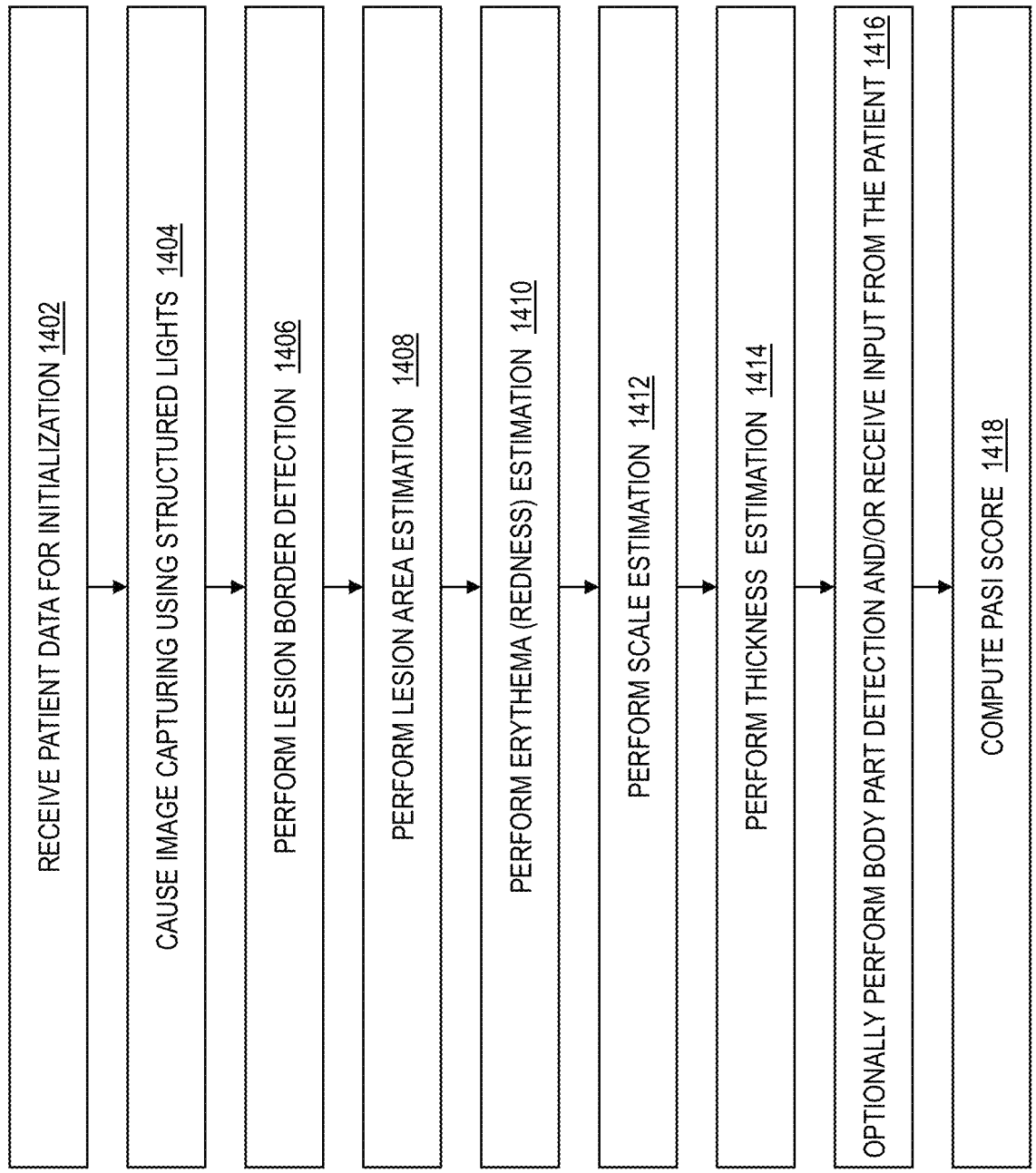
FIG. 14 is a flow diagram of a process for automatically determining skin disorder scoring using structured lights in accordance with one or more embodiments of the invention.

FIG. 14 illustrates a flow diagram of a process 1400 for automatically determining PASI scoring using structured light in accordance with one or more embodiments of the present invention. The process 1400 is performed by the system 1200 in FIGS. 12 and 13. At block 1402, one or more software applications 1310 of computer system 1202 are configured to be initialized by receiving a patient's data and storing that data in patient data 1306. As patient data 1306, the software application 1310 can receive the person's height, identification of the body part area(s) being scanned immediately prior to scanning, other measurements of the patient, previous data collected on the patient, etc. Some patient data 1306 can be input to the software application 1310 using an input device such as a touch screen, keyboard, mouse, etc. Additionally, benchmark data 1308 is provided to and/or pulled by the software application 1310 from a network 1350. The benchmark data 1308 is utilized for bench-marking the ratings that will be used. Benchmark data, also referred to as baseline data, is available from the person himself/herself, from other skin disorder patients (e.g., psoriasis patients) over the network 1350, and from a standardized psoriasis database over the network 1350. The network 1350 can be connected to various computers/servers to provide the benchmark data.

At block 1404, the software application 1310 is configured to cause image capturing to be performed by the device 1204 and computer system 1202 of system 1200. As the images 1304 captured and stored in computer system 1202, the cameras 1212 can capture RGB images (normal 2D color images) using structured lights along with 3D scanning images using structured lights. (For instance, the RGB images will be utilized to determine the light green from the dark green areas on the structured lights. The returned fringe pattern from the structured lights is used to make the 3D image.) The software application 1310 of the computer system 1202 is configured to instruct/cause the device 1204 to perform 3D scanning with structured lights to capture images 1304 for processing. The software application 1310 can communicate with one or more software applications 1340 to capture images and/or directly instruct/operate the device 1204 to capture images by 3D scanning with structured light as discussed herein.

When one light projector 1210 (e.g., projector A as shown in FIG. 12) is powered on to emit light, each of the cameras 1212 captures multiple images of the skin area and lesion 1250. The distance of device 1204 (and computer system 1202) of system 1200 (e.g., mobile device, such as a mobile phone) from the skin is determined using IR light emitted from and received by IR device 1214. Additionally, the height of the lesion 1250 (i.e., image height) can be detected using the formula below along with the determined distance of device 1204 (and computer system 1202) of system 1200 (e.g., mobile device, such as a mobile phone) from the skin which was detected using the IR device 1214. As one example, the altitude (i.e., height) can be determined by using the formula, for example, Real Object Height=(Distance to Object*Object Height on sensor (image height))/Focal length. Further, the altitude of the device 1204 (and computer system 1202) of system 1200 from the ground can be measured using a built-in sensor and/or altimeter (as readily available in, e.g., mobile devices, such as mobile phones). Accordingly, the software application 1310 can determine (and/or knows in advance) which body part is being captured, given that the height of the person is previously known in patient data 1306 by the software application 1310. In one or more embodiments, the software application 1310 can determine which body part is being captured by comparing the user's previously known height to the measured altitude of the device 1204 (when capturing the images) from the ground or relative to the floor. Additionally, the images (e.g., RGB image) of the whole lesion (W_l) is captured, and stored in images 1304.

The software application 1310 audibly asks (via speakers of the computer system 1202) the patient to continue moving or waving device 1204 around the lesion 1250 for a while to ensure that the system 1200 has captured enough images of the lesions 1250 with structured lights in different orientations on the lesion 1250. The software application 1310 can audibly inform the patient when to stop moving the device 1204 around the legion 1250, and/or audibly tell the patient to move the device 1204 of system 1200 at a slower rate in order to capture sufficient images of the lesion 1250. The device 1204 of system 1200 can automatically switch the projector and cameras as the user moves the system 1200 (e.g., mobile phone) around the lesion area 1250. For example, the pattern is projected onto the subject using an LCD projector and/or other stable light source, and then the system 1200 (camera) captures the shape of the pattern and calculates. This process is repeated as the user moves the system 1200.

The structured light projectors 1210 can be configured to project particular colored lights based on the patient's skin tone. For example, the software application 1310 can receive input of skin tone data by the patient and/or can extract skin tone data from patient data 1306. Additionally, the cameras 1212 can be utilized to capture images (which do not utilize structured lights) of the patient, and the software application 1310 can determine the skin tone from the image. Based on the skin tone, the software application 1310 is configured to select at least one color for the structured lights (and can utilize one color for the first round of 3D scanning, and utilize a different second color for the second round of 3D scanning). In some cases, green structured lights can be utilized for light skin tones and red structured light can be utilized for browner skin tones.

The light projectors 1210 can use LED light as well as laser light to project different types of structured lights as needed. For example, to measure thickness of a microstructure on the skin, gray scale laser illumination is usually used for better accuracy. On the other hand for erythema detection, RGB LED is sufficient, but colored laser illumination can also be used.

Figure 15:
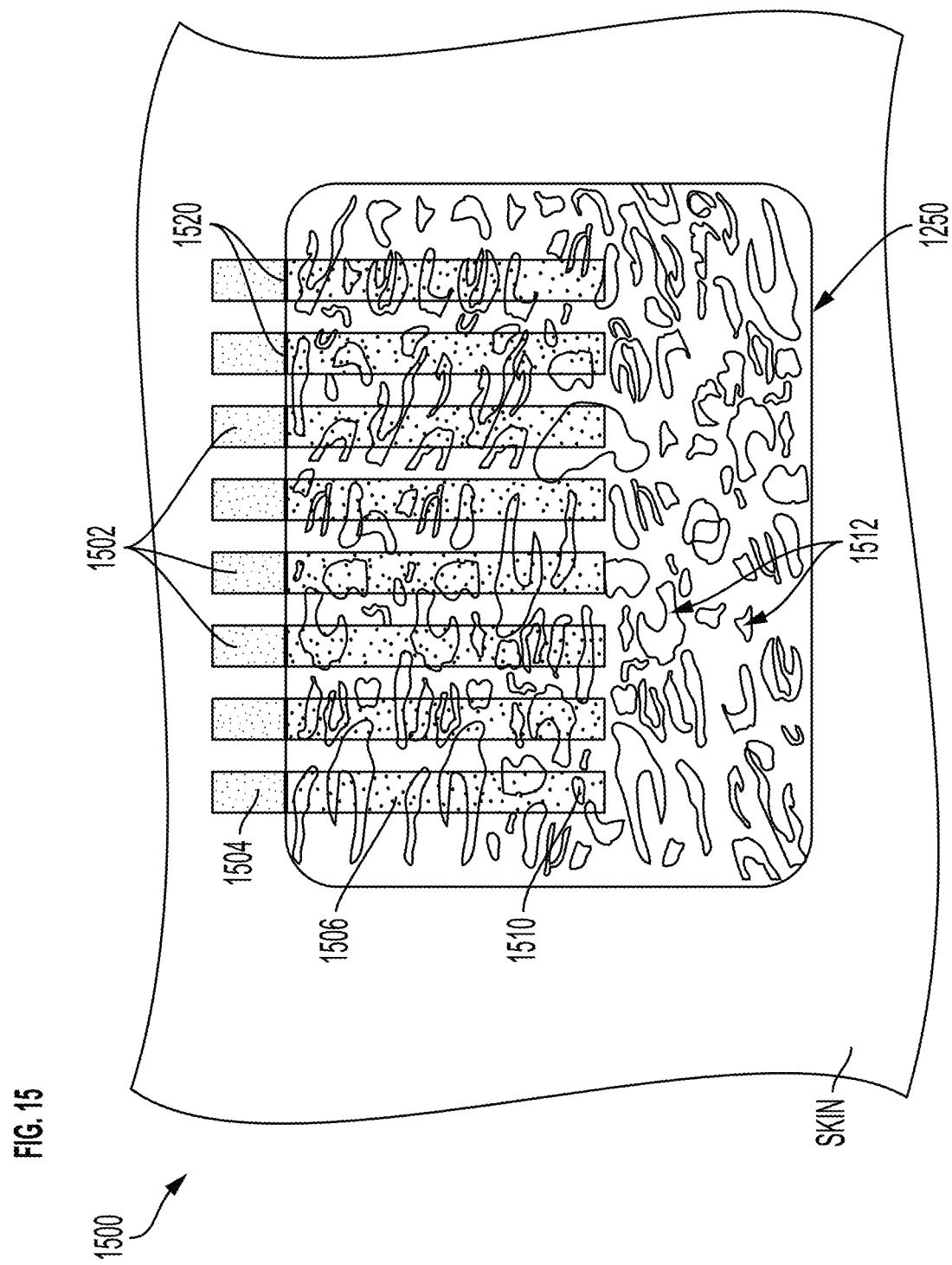
FIG. 15 illustrates an image representing a lesion captured with colored structured lights according to one or more embodiments of the invention.

Returning back to FIG. 14, at block 1406, the software application 1310 is configured to perform lesion border detection of the one or more lesions 1250. FIG. 15 illustrates an image 1500 of example lesion 1250 captured with colored structured lights 1502 according to one or more embodiments of the invention. In this example, the structured lights 1502 are green in a vertical pattern. The structured lights can be in other patterns and are not limited to vertical lines spaced apart, although the vertical line pattern for structured lights can be used to beneficially provide a 3D image of the lesion on skin. The software application 1310 is configured to identify lesion border points using chromatic differences in the structured lights 1502, as shown in FIG. 15, and compute the lesion border 1520 from the border points previously detected. For example, the portions of the structured lights 1502 that fall on (i.e., cover) the normal skin having no lesion have a reference color 1504, which is green for the structured lights 1502 in this example. The portions of the structured lights 1502 that fall on the lesion 1250 have a different shade (and/or different color), which is darker color, and represent detected color segments 1506 of the lesion 1250. In this example, the red color of the lesion 1250 combined with the green color of the structured lights 1502 results in the darker green color of the detected color segments 1506 compared to the lighter green reference color 1504 of the structured lights 1502. The border points are detected at the junction of the lighter green reference color 1504 and the darker detected color segments 1506 for each of the structured lights 1502. The software application 1310 can connect the border points in the image 1500 (and/or from multiple images of the lesion and surrounding normal skin) to determine the border 1520 encircling the lesion 1250.

At block 1408, the software application 1310 is configured to perform lesion area estimation. Using the distance D from camera, the camera's focal length, and angle, the software application 1310 can estimate the size of the lesion area 1250 on the focal plane of the camera. The IR device 1214 can have a camera (i.e., sensor) for detecting the returned IR signal, and/or camera C could be utilized.

At block 1410, the software application 1310 is configured to perform erythema (redness) estimation. The software application 1310 is configured to measure chromatic differences (i.e., color differences) along the structured light projections within the lesion border 1520. FIG. 5 only shows an upper part of the border 1520 for conciseness but it should be appreciated that the border 1520 encircles the entire legion 1250. The software application 1310 is configured to compute the average value of the chromatic differences and compare the computed average value with a benchmark value (in benchmark data 1308) to compute a severity score erythema (redness). This tells how much of the detected color segments 1506 have changed to a darker green color because of the red legion underneath.

At block 1412, the software application 1310 is configured to perform scale (scaliness, scaling, and/or desquamation) estimation. The software application 1310 is configured to detect scales 1512 within the lesion area 1250 (i.e., within the border 1520). The software application 1310 can use a segmentation algorithm to determine the lighter green, represented as detected scales 1510, within the detected color segments 1506 of structured lights 1502, to estimate the intensity of scales or white pieces of skin that are present. The software application 1310 is configured to count detected scales 1510, compute average chromatic of the detected scales 1510, and compare the average chromatic value with the benchmark value to compute scale severity. Along with the average value, other measures can be computed such as number of detected scales, size of scales, chromatic variance, etc. The measures can be compared with benchmark values, separately or combined, to compute the scale severity.

At block 1414, the software application 1310 is configured to perform thickness estimation. Because the device 1204 uses 3D scanning with structured lights, the captured images inherently provide thickness information in the returned fringe pattern, which can be utilized to measure/discern thickness to a depth of about a micrometer. The software application 1310 is configured to detect thickness by comparing the 3D captured images of the skin with the estimated lesion area within the border 1520.

At block 1416, the software application 1310 is configured to optionally perform body part detection and/or the software application 1310 can request and receive input from the patient of the body part being imaged. Using the altitude (height) of the device 1204 and computer system 1202 of system 1200 (e.g., mobile phone) when capturing the image and using the patient's known height in patient data 1306, the software application 1310 is configured to detect the body part of the lesion 1250. For example, the detection determines whether the captured image belongs to the head, upper limbs, lower limbs, or trunk. However, this procedure is optional since the patient can go to a clinic, and overall assessment and body parts are measured. Accordingly, this clinical data can be stored in patient data 1306 and used later for the PASI score.

At block 1418, the software application 1310 is configured to compute the PASI score for the patient. The software application 1310 uses the previously estimated area, thickness, erythema severity, and scale severity to compute the PASI score.

For explanation purposes and not limitation, an example scenario is provided below, which further explains how the system 200 works for a patient. Under preliminaries and assumptions, initial setup will include storing (e.g., by software application 1310 in database 1312) the skin area for each of upper-limbs (U), lower-limbs (L) and trunk (T) that will be estimated by the dermatologist (tot__A_u, tot_A_l, tot__A_t), where tot_A_u is total area upper-limbs, tot__A_l is total area lower-limbs, and tot__A_t is total area trunk, which refer to the surface area of a particular body part. To use the system 1200, the patient will scan the skin lesions all over the body using software application 1310 (which can control device 1204 directly and/or via software application 1340). The software application 1310 groups the images by body part (i.e., upper-limbs (U), lower-limps (L), and trunk (T)), and then calculates area (A), scaliness (S), erythema (E), and induration (I) for each region, as will be discussed further below. It is also assumed that the PASI measurements for the head region will be entered manually to the system 1200 by, for example, a dermatologist because hair is assumed to cover the lesion on the scalp. In cases where the patient has little to no hair on the scalp and/or when the lesion is not obscured by hair, the system 1200 can process the head as discussed herein for other body parts; accordingly, the body part for the head would be designated (H).

Now proceeding to measurements made using the software application 1310, this example scenario assumes that the patient has a total of 9 lesions where 2 are in the upper limbs, 4 are in the lower limbs, and 3 are in the trunk areas. Therefore, the software application 1310 of system 1200 will allow the patient to complete 4 PASI measures (which are A (area), I (induration), E (erythema), and S (scales)) for each of the 9 lesions separately through the following operations. Although 9 lesions are given in the example scenario, it should be appreciated that the system 200 can be applied to person having a single lesion or more than one lesion.

For body_part detection, the software application 1310 of system 1200 is configured to detect the body part for each lesion image using the altitude of the camera 1212 of system 1200 with respect to the ground and the patient's height from patient data 1306. Based on the altitude of the system 1200, the software application 1310 selects the corresponding total area from the database 1312 (e.g., tot_A_u for a lesion on the upper limb). In some cases, the person can input the corresponding area (selection of the body part e.g., tot_A_u for a lesion on the upper limb) in software application 1310 for the one or more lesions in that particular area.

For determining the area_score (A), the software application 1310 of system 1200 is configured to segment the lesion by tracking the difference in original reflected green color to extract the lesion border. For example, if the original green light's color value was #CCFFCC when emitted from device 1204 and the reflected green on the lesion image was detected as #99FF99 on certain section (i.e., border part) of the fringe, that would represent the border of the lesion in that fringe. The vertical lines of the structured lights are each a single fringe. Once the border is detected in each fringe of the structured light, the software application 1310 of system 1200 maps the border 1520 of the lesion 1250 in the RGB image (W_I) of the lesion. The chromatic values in the RGB space will be used for severity assessment. This is not limited to RGB space, and could be any other captured color space, such as YCbCr (where Y is the luma component, CB is the blue-difference component, and CR is the red-difference chroma component). The lesion area (A_C) is then calculated by software application 1310 by counting the number of pixels inside the lesion border.

The percent of the skin lesion be calculated using the formula: (A_C/A tot)*100, where A_tot is total area of the particular body part. A_tot is a generic way or variable for representing any one of tot__A_u, tot_A_l, tot__A_t. The area_score (A) is then calculated based on the computed percentage, where nil percent means area_score 0, where 1-9% denotes area score 1, where 10-29% denotes area score 2, where 30-49% denotes area score 3, where 50-69% denotes area score 4, where 70-89% denotes area score 5, and where 90-100% denotes area score 6.

For determining the induration_score (I), the software application 1310 of system 1200 is configured to calculate the lesion induration (i.e., thickness which is I_val) using the structured lights. The measured thickness value I_val (e.g., 2 millimeters (mm)) can be passed to a model 1314, for example, a linear regression model, that maps the I_val to an induration_score (I) between 0 and 4.

For determining the scale_score, the software application 1310 of system 1200 is configured to segment the image using, for example, a thresholding technique because scales will have lighter green color (i.e., scales are white). For example, if the original green light's color value was #CCFFCC for the structured lights (e.g., light green/shade of the reference color 1504), and then any image area with green color lighter than #CCFFCC will represent the scales (e.g., detected scales 1510). After the pixels associated with the scales are detected, the software application 1310 of system 1200 computes the average green value (S_color, which is the average scale color value) of those pixels. Once the average green value (S_color) across the scales are computed, the S_color value can be passed to the model 1314, for example, a linear regression model that maps the S_color value to a scale_score (S) between 0 and 4.

For determining the erythema_score (E), the software application 1310 of system 1200 is configured to use the non-scales pixels within the lesion area for consideration as erythema score and calculate the average value (E_color, which is the average erythema color value) of those non-scales pixels. The E_color value is then passed to the model 1314, for example, a linear regression model that maps E_color value to an erythema_score (E) between 0 and 4.

For determining the PASI_score, the software application 1310 of system 1200 is configured to combine the computed PASI measures that belong to same body region/location by averaging across the lesions in a particular body area. So, instead of 4 measures*9 images, it will be 4 measures*3 body regions (equaling 12 measurements) for the example scenario above. Accordingly, the example values are as follows:

A_u: Lesion area score for upper limb;
E_u: Lesion erythema score for upper limb;
I_u: Lesion induration score for upper limb;
S_u: Lesion scale score for upper limb;
A_l: Lesion area score for lower limb;
E_l: Lesion erythema score for lower limb;
I_l: Lesion induration score for lower limb;
S_l: Lesion scale score for lower limb;
A_t: Lesion area score for trunk;
E_t: Lesion erythema score for trunk;
I_t: Lesion induration score for trunk; and
S_t: Lesion scale score for trunk.

The software application 1310 of system 1200 is configured to calculate the final PASI score from the above 12 calculated values using the following equation: PASI_Score=head_score (manually entered by dermatologist or possibly determined)+0.2*A_u*(E_u+I_u+S_u)+0.3*A_t*(E_t+I_t+S_t)+0.4*A_l*(E_l+I_l+S_l). In one or more embodiments of the invention, instead of manually entering or receiving the head_score, the head_score for the patient is determined by 0.1*A_h*(E_h+I_h+S_h), where A_h is the lesion area score for head, E_h is the lesion erythema score for the head, I_h is the lesion induration score for head, and S_h is the lesion scale score for upper limb.

Figure 16:
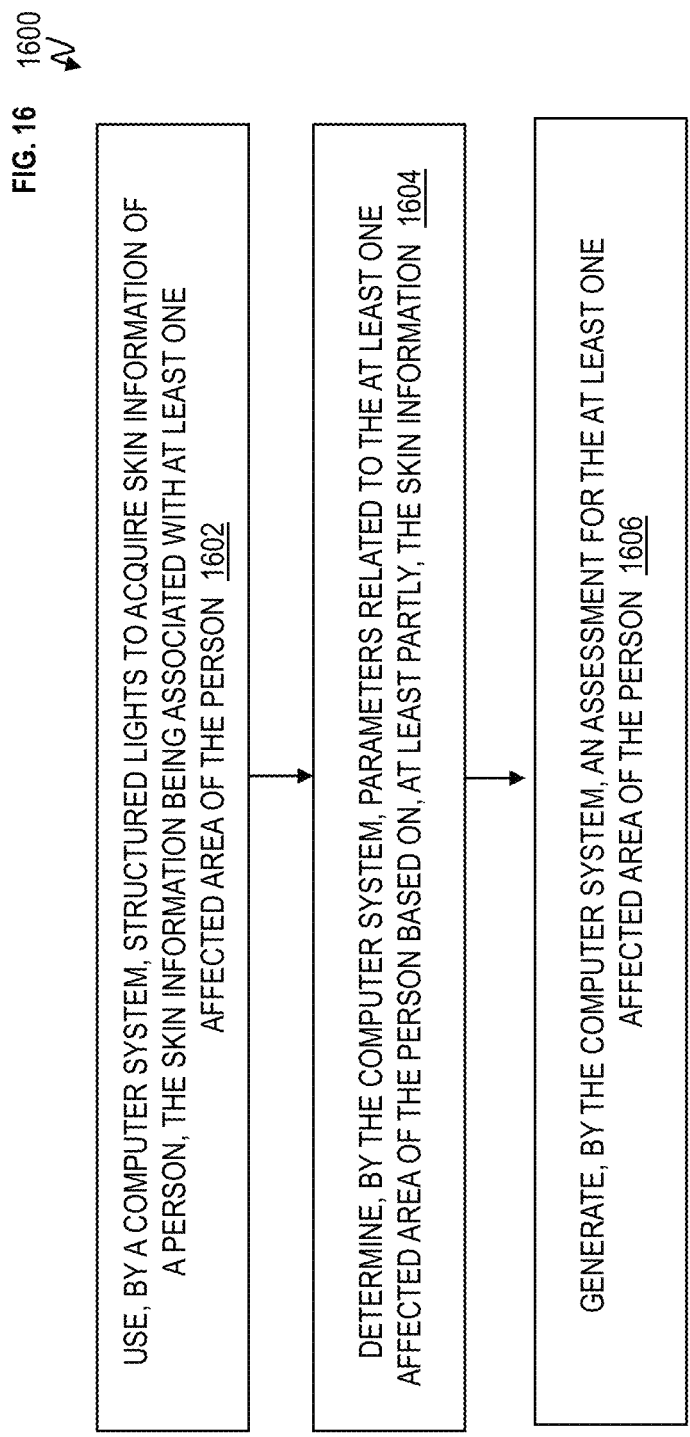
FIG. 16 is a flow diagram of a computer-implemented method using structured lights to determine skin disorder severity assessment according to one or more embodiments of the invention.

FIG. 16 is a flow diagram of a computer-implemented method 1600 using structured lights to determine psoriasis severity assessment (e.g., PASI score) according to embodiments of the invention. At block 1602, the computer system 202 is configured to use (and/or can cause/instruct the device 1204 to use) structured lights (e.g., one or more different colored light patterns) to acquire skin information of a person, the skin information being associated with at least one affected area (e.g., there can be various lesions 1250 on the body) of the person. At block 1604, the computer system 202 is configured to determine parameters related to the at least one affected area of the person based on, at least partly, the skin information. At block 1606, the computer system 202 is configured to generate an assessment for the at least one affected area of the person.

A border (e.g., border 1520) of the at least one affected area is determined based on the skin information. A chromatic change in the structured lights (e.g., the chromatic change from light green/shade of the reference color 1504 to the darker color/shade of detected color segments 1506) provides skin information for the at least one affected area. A three-dimensional (3D) image (of the lesion 1250 and surrounding normal skin) is obtained by using the structured lights.

The parameters related to the at least one affected area of the person include an area value (e.g., area score (A), surface area of lesion (i.e. number of lesion pixels)). The parameters related to the at least one affected area of the person include an induration value (e.g., induration score (I)). The parameters related to the at least one affected area of the person include a scale value (e.g., scale score (S)). The parameters related to the at least one affected area of the person include an erythema value (e.g., erythema score (E)). The assessment for the at least one affected area of the person is a psoriasis severity assessment (e.g., determining of a PASI score for the person).

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
    using, by a computer system, structured lights to acquire skin information, the skin information being associated with at least one affected area of skin;
    determining, by the computer system, parameters related to the at least one affected area of the skin based, at least partly, on the skin information, the computer system using a first trained model to determine an epidermal inflammation, a vessel morphology, a keratinocyte morphology, and a proliferation of keratinocytes of the at least one affected area of the skin based on a three-dimensional (3D) image of the at least one affected area of the skin, wherein a second trained model is trained on two-dimensional (2D) images to generate an area value, a scale value, and an erythema value of the at least one affected area of the skin; and
    generating, by the computer system, an assessment for the at least one affected area of the skin based on the first trained model and the second trained model.

2. The computer-implemented method of claim 1, wherein a border of the at least one affected area is determined based on the skin information.

3. The computer-implemented method of claim 1, wherein a chromatic change in the structured lights provides the skin information for the at least one affected area.

4. The computer-implemented method of claim 1, wherein the three-dimensional (3D) image is obtained using the structured lights.

5. The computer-implemented method of claim 1, wherein the assessment for the at least one affected area comprises a psoriasis severity assessment.

6. A system comprising:
    a memory having computer readable instructions; and
    one or more processors for executing the computer readable instructions, the computer readable instructions controlling the one or more processors to perform operations comprising:
        using structured lights to acquire skin information, the skin information being associated with at least one affected area of skin;
        determining parameters related to the at least one affected area of the skin based, at least partly, on the skin information, wherein a first trained model is used to determine an epidermal inflammation, a vessel morphology, a keratinocyte morphology, and a proliferation of keratinocytes of the at least one affected area of the skin based on a three-dimensional (3D) image of the at least one affected area of the skin, wherein a second trained model is trained on two-dimensional (2D) images to generate an area value, a scale value, and an erythema value of the at least one affected area of the skin; and generating an assessment for the at least one affected area of the skin based on the first trained model and the second trained model.

7. The system of claim 6, wherein a border of the at least one affected area is determined based on the skin information.

8. The system of claim 6, wherein a chromatic change in the structured lights provides the skin information for the at least one affected area.

9. The system of claim 6, wherein the three-dimensional (3D) image is obtained using the structured lights.

10. The system of claim 6, wherein the assessment for the at least one affected area comprises a psoriasis severity assessment.

11. A computer program product comprising a computer readable storage medium having program instructions embodied therewith, the program instructions executable by a processor to cause the processor to perform operations comprising:

using structured lights to acquire skin information, the skin information being associated with at least one affected area of skin;

determining parameters related to the at least one affected area of the skin based, at least partly, on the skin information, wherein a first trained model is used to determine an epidermal inflammation, a vessel morphology, a keratinocyte morphology, and a proliferation of keratinocytes of the at least one affected area of the skin based on a three-dimensional (3D) image of the at least one affected area of the skin, wherein a second trained model is trained on two-dimensional (2D) images to generate an area value, a scale value, and an erythema value of the at least one affected area of the skin; and generating an assessment for the at least one affected area of the skin based on the first trained model and the second trained model.

12. The computer program product of claim 11, wherein a border of the at least one affected area is determined based on the skin information.

13. The computer program product of claim 11, wherein a chromatic change in the structured lights provides the skin information for the at least one affected area.

\* \* \* \* \*